(12) United States Patent
Bierman

(10) Patent No.: US 11,712,543 B2
(45) Date of Patent: *Aug. 1, 2023

(54) VASCULAR ACCESS DEVICE

(71) Applicant: SMITHS MEDICAL ASD, INC., Plymouth, MN (US)

(72) Inventor: Steven F. Bierman, Del Mar, CA (US)

(73) Assignee: SMITHS MEDICAL ASD, INC., Plymouth, MN (US)

( * ) Notice: Subject to any disclaimer, the term of this patent is extended or adjusted under 35 U.S.C. 154(b) by 146 days.

This patent is subject to a terminal disclaimer.

(21) Appl. No.: 17/314,545

(22) Filed: May 7, 2021

(65) Prior Publication Data

US 2021/0260343 A1 Aug. 26, 2021

Related U.S. Application Data

(63) Continuation of application No. 15/568,765, filed as application No. PCT/US2016/027972 on Apr. 15, 2016, now Pat. No. 11,027,099.

(Continued)

(51) Int. Cl.
*A61M 25/06* (2006.01)
*A61M 39/02* (2006.01)
(Continued)

(52) U.S. Cl.
CPC .... *A61M 25/0606* (2013.01); *A61M 25/0668* (2013.01); *A61M 25/0693* (2013.01);
(Continued)

(58) Field of Classification Search
CPC .......... A61M 25/0606; A61M 25/0668; A61M 25/0693; A61M 39/0247; A61M 25/0097;
(Continued)

(56) References Cited

U.S. PATENT DOCUMENTS 1,436,882 A 11/1922 Knepper
3,185,152 A 5/1965 Ring
(Continued)

FOREIGN PATENT DOCUMENTS

DE 2052364 A1 4/1972
DE 8915299 U1 2/1990
(Continued)

OTHER PUBLICATIONS

Final Decision of Rejection dated Jan. 4, 2021 for Japanese Application No. 2017-556650, 7 pages.
(Continued)

*Primary Examiner* — Theodore J Stigell
(74) *Attorney, Agent, or Firm* — Benesch, Friedlander, Coplan & Aronoff LLP

(57) ABSTRACT

An access device for placing a medical article within a body space includes a syringe, a needle, and a sheath which are employed together with a guide wire. The sheath can be coaxially and slideably disposed about the needle. During insertion of the sheath over the needle, guide wire and into the body space, the syringe provides a negative pressure to ensure that any air located between the inside diameter of the sheath and the outside diameter of the needle is drawn into the needle rather than into the body space. In certain embodiments, a dilator is coaxially and slideably disposed about the needle and within the sheath.

22 Claims, 34 Drawing Sheets

Related U.S. Application Data

(60) Provisional application No. 62/209,841, filed on Aug. 25, 2015, provisional application No. 62/155,368, filed on Apr. 30, 2015.

(51) Int. Cl.
*A61M 39/06* (2006.01)
*A61M 25/00* (2006.01)
*A61M 25/09* (2006.01)

(52) U.S. Cl.
CPC ..... *A61M 39/0247* (2013.01); *A61M 25/0097* (2013.01); *A61M 25/09041* (2013.01); *A61M 2025/0687* (2013.01); *A61M 2039/0258* (2013.01); *A61M 2039/0273* (2013.01); *A61M 2039/0291* (2013.01); *A61M 2039/062* (2013.01)

(58) Field of Classification Search
CPC .... A61M 25/09041; A61M 2025/0687; A61M 2039/0258; A61M 2039/0273; A61M 2039/0291; A61M 2039/062; A61M 39/02; A61M 39/06
See application file for complete search history.

(56) References Cited

U.S. PATENT DOCUMENTS

| | | | |
|---|---|---|---|
| 3,539,034 | A | 11/1970 | Tafeen |
| 3,540,447 | A | 11/1970 | Howe et al. |
| 3,565,074 | A | 2/1971 | Foti et al. |
| 3,670,729 | A | 6/1972 | Bennett et al. |
| 3,680,562 | A | 8/1972 | Wittes |
| 3,993,079 | A | 11/1976 | Gatztanondo |
| 3,995,628 | A | 12/1976 | Gula et al. |
| 4,052,989 | A | 10/1977 | Kline |
| 4,068,659 | A | 1/1978 | Moorehead |
| 4,068,660 | A | 1/1978 | Beck |
| 4,072,146 | A | 2/1978 | Howes |
| 4,170,993 | A | 10/1979 | Alvarez |
| 4,180,068 | A | 12/1979 | Jacobsen et al. |
| 4,191,186 | A | 3/1980 | Keeler |
| 4,192,305 | A | 3/1980 | Seberg |
| 4,205,675 | A | 6/1980 | Vaillancourt |
| 4,230,109 | A | 10/1980 | Geiss |
| 4,230,123 | A | 10/1980 | Hawkins, Jr. |
| 4,233,974 | A | 11/1980 | Desecki et al. |
| 4,274,408 | A | 6/1981 | Nimrod |
| 4,333,505 | A | 6/1982 | Jones et al. |
| 4,345,596 | A | 8/1982 | Young |
| 4,411,655 | A | 10/1983 | Schreck |
| 4,412,832 | A | 11/1983 | Kling et al. |
| 4,417,886 | A | 11/1983 | Frankhouser et al. |
| 4,445,893 | A | 5/1984 | Bodicky |
| 4,512,351 | A | 4/1985 | Pohndorf |
| 4,525,157 | A | 6/1985 | Vaillancourt |
| 4,539,003 | A | 9/1985 | Tucker |
| 4,581,019 | A | 4/1986 | Curelaru et al. |
| 4,610,665 | A | 9/1986 | Matsumoto et al. |
| 4,629,450 | A | 12/1986 | Susuki et al. |
| 4,652,256 | A | 3/1987 | Vaillancourt |
| 4,655,750 | A | 4/1987 | Vaillancourt |
| 4,661,300 | A | 4/1987 | Daugherty |
| 4,752,292 | A | 6/1988 | Lopez et al. |
| 4,772,264 | A | 9/1988 | Cragg |
| 4,791,937 | A | 12/1988 | Wang |
| 4,826,486 | A | 5/1989 | Palsrok et al. |
| 4,850,960 | A | 7/1989 | Grayzel |
| 4,850,975 | A | 7/1989 | Furukawa |
| 4,869,259 | A | 9/1989 | Elkins |
| 4,894,052 | A | 1/1990 | Crawford |
| 4,917,669 | A | 4/1990 | Bonaldo |
| 4,917,679 | A | 4/1990 | Kronner |
| 4,944,728 | A | 7/1990 | Carrell |
| 4,950,252 | A | 8/1990 | Luther et al. |
| 4,952,207 | A | 8/1990 | Lemieux |
| 4,955,890 | A | 9/1990 | Yamamoto et al. |
| 4,961,729 | A | 10/1990 | Vaillancourt |
| 4,963,306 | A | 10/1990 | Weldon |
| 4,978,334 | A | 12/1990 | Toye et al. |
| 4,995,866 | A | 2/1991 | Amplatz et al. |
| 4,997,421 | A | 3/1991 | Palsrok et al. |
| 5,045,065 | A * | 9/1991 | Raulerson ........... A61M 25/065 604/236 |
| 5,049,136 | A | 9/1991 | Johnson |
| 5,053,017 | A | 10/1991 | Chamuel |
| 5,059,186 | A | 10/1991 | Yamamoto |
| 5,064,414 | A | 11/1991 | Revane |
| 5,066,284 | A | 11/1991 | Mersch et al. |
| 5,067,945 | A | 11/1991 | Ryan et al. |
| 5,098,389 | A | 3/1992 | Cappucci |
| 5,098,392 | A | 3/1992 | Fleischhacker et al. |
| 5,102,394 | A | 4/1992 | Lasaitis et al. |
| 5,105,807 | A | 4/1992 | Kahn et al. |
| 5,108,374 | A | 4/1992 | Lemieux |
| 5,112,308 | A | 5/1992 | Olsen et al. |
| 5,114,401 | A | 5/1992 | Stuart et al. |
| 5,135,502 | A | 8/1992 | Koenig, Jr. et al. |
| 5,135,505 | A | 8/1992 | Kaufman |
| 5,158,544 | A | 10/1992 | Weinstein |
| 5,167,637 | A | 12/1992 | Okada et al. |
| 5,171,218 | A | 12/1992 | Fonger et al. |
| 5,215,525 | A | 6/1993 | Sturman |
| 5,215,528 | A | 6/1993 | Purdy et al. |
| 5,242,410 | A | 9/1993 | Melker |
| 5,242,414 | A | 9/1993 | Fischell et al. |
| 5,242,427 | A | 9/1993 | Bilweis |
| 5,246,426 | A | 9/1993 | Lewis et al. |
| 5,248,306 | A | 9/1993 | Clark et al. |
| 5,250,038 | A | 10/1993 | Melker et al. |
| 5,255,691 | A | 10/1993 | Otten |
| 5,279,590 | A | 1/1994 | Sinko et al. |
| 5,295,969 | A | 3/1994 | Fischell |
| 5,295,970 | A | 3/1994 | Clinton et al. |
| 5,306,253 | A | 4/1994 | Brimhall |
| 5,312,355 | A | 5/1994 | Lee |
| 5,312,359 | A | 5/1994 | Wallace |
| 5,314,411 | A | 5/1994 | Bierman et al. |
| 5,328,480 | A | 7/1994 | Melker et al. |
| 5,330,433 | A | 7/1994 | Fonger et al. |
| 5,334,149 | A | 8/1994 | Nortman et al. |
| 5,334,157 | A | 8/1994 | Klein et al. |
| 5,336,191 | A | 8/1994 | Davis et al. |
| 5,342,315 | A | 8/1994 | Rowe et al. |
| 5,366,441 | A | 11/1994 | Crawford |
| 5,380,290 | A | 1/1995 | Makower et al. |
| 5,388,589 | A | 2/1995 | Davis |
| 5,391,152 | A | 2/1995 | Patterson |
| 5,391,178 | A | 2/1995 | Vapor |
| 5,397,311 | A | 3/1995 | Walker et al. |
| 5,403,283 | A | 4/1995 | Luther |
| 5,419,766 | A | 5/1995 | Chang et al. |
| 5,425,718 | A | 6/1995 | Tay et al. |
| 5,468,024 | A | 11/1995 | Carman et al. |
| 5,512,052 | A | 4/1996 | Jesch |
| 5,520,654 | A | 5/1996 | Wahlberg |
| 5,531,701 | A | 7/1996 | Luther |
| 5,531,713 | A | 7/1996 | Mastronardi et al. |
| 5,542,932 | A | 8/1996 | Daugherty |
| 5,562,634 | A | 10/1996 | Flumene et al. |
| 5,578,083 | A | 11/1996 | Laguette et al. |
| 5,589,120 | A | 12/1996 | Khan et al. |
| 5,676,653 | A | 10/1997 | Taylor et al. |
| 5,676,658 | A | 10/1997 | Erskine |
| 5,676,689 | A | 10/1997 | Kensery et al. |
| 5,685,856 | A | 11/1997 | Lehrer |
| 5,688,249 | A | 11/1997 | Chang et al. |
| 5,688,570 | A | 11/1997 | Ruttinger |
| 5,690,619 | A | 11/1997 | Erskine |
| 5,704,914 | A | 1/1998 | Stocking et al. |
| 5,712,229 | A | 1/1998 | Hopkins et al. |
| 5,713,876 | A | 2/1998 | Bogert |
| 5,728,132 | A | 3/1998 | Van Tassel et al. |

(56) References Cited

U.S. PATENT DOCUMENTS

| | | |
|---|---|---|
| 5,749,857 A | 5/1998 | Guppy |
| 5,755,693 A | 5/1998 | Walker et al. |
| 5,795,339 A | 8/1998 | Erskine |
| 5,810,780 A | 9/1998 | Brimhall et al. |
| 5,820,596 A | 10/1998 | Rosen et al. |
| 5,820,606 A | 10/1998 | Davis |
| 5,827,202 A | 10/1998 | Miraki et al. |
| 5,830,190 A | 11/1998 | Howell |
| 5,833,662 A | 11/1998 | Stevens |
| 5,853,393 A | 12/1998 | Bogert |
| 5,858,002 A | 1/1999 | Jesch |
| 5,858,007 A | 1/1999 | Fagan et al. |
| 5,865,806 A | 2/1999 | Howell |
| 5,873,854 A | 2/1999 | Wolvek |
| 5,885,217 A | 3/1999 | Gisselberg et al. |
| 5,885,253 A | 3/1999 | Liu |
| 5,902,254 A | 5/1999 | Magram |
| 5,904,657 A | 5/1999 | Unsworth et al. |
| 5,910,132 A | 6/1999 | Schultz |
| 5,919,160 A | 7/1999 | Sanfilippo |
| 5,935,110 A | 8/1999 | Brimhall |
| 5,951,518 A | 9/1999 | Licata et al. |
| 5,954,708 A | 9/1999 | Lopez et al. |
| 5,957,894 A | 9/1999 | Kerwin et al. |
| 5,984,895 A | 11/1999 | Padilla et al. |
| 6,004,294 A | 12/1999 | Brimhall et al. |
| 6,027,480 A | 2/2000 | Davis et al. |
| 6,046,143 A | 4/2000 | Khan et al. |
| 6,074,377 A | 6/2000 | Sanfilippo |
| 6,080,141 A | 6/2000 | Castro et al. |
| 6,083,207 A | 7/2000 | Heck |
| 6,117,108 A | 9/2000 | Woehr et al. |
| 6,117,140 A | 9/2000 | Munsinger |
| 6,120,494 A | 9/2000 | Jonkman |
| 6,137,468 A | 10/2000 | Martinez et al. |
| 6,156,010 A | 12/2000 | Kuracina et al. |
| 6,159,179 A | 12/2000 | Simonson |
| 6,179,813 B1 | 1/2001 | Ballow et al. |
| 6,210,366 B1 | 4/2001 | Sanfilippo |
| 6,221,050 B1 | 4/2001 | Ishida |
| 6,245,044 B1 | 6/2001 | Daw et al. |
| 6,273,871 B1 | 8/2001 | Davis et al. |
| 6,277,100 B1 | 8/2001 | Raulerson |
| 6,287,278 B1 | 9/2001 | Woehr et al. |
| 6,287,322 B1 | 9/2001 | Zhu et al. |
| 6,328,717 B1 | 12/2001 | Solomon et al. |
| 6,336,914 B1 | 1/2002 | Gillsespie, III |
| 6,379,333 B1 | 4/2002 | Brimhall et al. |
| 6,436,070 B1 | 8/2002 | Botich et al. |
| 6,461,362 B1 | 10/2002 | Halseth et al. |
| 6,475,207 B1 | 11/2002 | Maginot |
| 6,488,662 B2 | 12/2002 | Sirimanne |
| 6,500,152 B1 | 12/2002 | Illi |
| 6,524,277 B1 | 2/2003 | Chang |
| 6,567,101 B1 | 5/2003 | Thomas |
| 6,569,120 B1 | 5/2003 | Green et al. |
| 6,602,240 B2 | 8/2003 | Hermann et al. |
| 6,607,353 B2 | 8/2003 | Masutani |
| 6,607,511 B2 | 8/2003 | Halseth et al. |
| 6,626,868 B1 | 9/2003 | Prestidge et al. |
| 6,641,564 B1 | 11/2003 | Kraus |
| 6,692,462 B2 | 2/2004 | MacKenzie et al. |
| 6,692,482 B2 | 2/2004 | Heller et al. |
| 6,695,816 B2 | 2/2004 | Cassidy |
| 6,712,789 B1 | 3/2004 | Lange et al. |
| 6,714,809 B2 | 3/2004 | Lee et al. |
| 6,719,772 B2 | 4/2004 | Trask et al. |
| 6,726,659 B1 | 4/2004 | Stocking et al. |
| 6,749,588 B1 | 6/2004 | Howell et al. |
| 6,783,516 B2 | 8/2004 | D'Heeron et al. |
| 6,786,875 B2 | 9/2004 | Barker et al. |
| 6,808,520 B1 | 10/2004 | Fourkas |
| 6,836,687 B2 | 12/2004 | Kelley |
| 6,905,481 B2 | 6/2005 | Sirimanne |
| 6,940,092 B2 | 9/2005 | Koshida et al. |
| 6,942,671 B1 | 9/2005 | Smith |
| 6,972,002 B2 | 12/2005 | Thorne |
| 6,994,693 B2 | 2/2006 | Tal |
| 7,001,396 B2 | 2/2006 | Glazier et al. |
| 7,025,746 B2 | 4/2006 | Tal |
| 7,083,626 B2 | 8/2006 | Hart et al. |
| 7,101,353 B2 | 9/2006 | Lui et al. |
| 7,109,967 B2 | 9/2006 | Hioki et al. |
| 7,163,525 B2 | 1/2007 | Franer |
| 7,182,755 B2 | 2/2007 | Tal |
| 7,192,433 B2 | 3/2007 | Osypka et al. |
| 7,196,689 B2 | 3/2007 | Moriyama |
| 7,226,434 B2 | 6/2007 | Carlyon et al. |
| 7,270,649 B2 | 9/2007 | Fitzgerald |
| 7,455,660 B2 | 11/2008 | Schweikert et al. |
| 7,458,954 B2 | 12/2008 | Ferguson et al. |
| 7,500,965 B2 | 3/2009 | Menzi et al. |
| 7,503,596 B2 | 3/2009 | Rome et al. |
| 7,544,184 B2 | 6/2009 | Cope |
| 7,556,617 B2 | 7/2009 | Voorhees, Jr. et al. |
| 7,614,123 B2 | 11/2009 | Schweikert |
| 7,670,316 B2 | 3/2010 | Windheuser et al. |
| 7,682,339 B2 | 3/2010 | Fujii |
| 7,717,878 B2 | 5/2010 | Smith |
| 7,722,567 B2 | 5/2010 | Tal |
| 7,744,569 B2 | 6/2010 | Smith |
| 7,827,656 B2 | 11/2010 | Schweikert |
| 7,833,202 B2 | 11/2010 | Suzuki |
| 7,922,696 B2 | 4/2011 | Tal et al. |
| 7,972,307 B2 | 7/2011 | Kraus et al. |
| 7,993,305 B2 | 8/2011 | Ye et al. |
| 8,021,338 B2 | 9/2011 | Adams |
| 8,070,750 B2 | 12/2011 | Wenstrom, Jr. et al. |
| 8,105,286 B2 | 1/2012 | Anderson et al. |
| 8,105,288 B2 | 1/2012 | Keyser et al. |
| 8,192,402 B2 | 6/2012 | Anderson et al. |
| 8,202,251 B2 | 6/2012 | Bierman et al. |
| 8,211,087 B2 | 7/2012 | Carter et al. |
| 8,377,006 B2 | 2/2013 | Tal et al. |
| 8,545,533 B2 | 10/2013 | Spenser et al. |
| 8,628,497 B2 | 1/2014 | Finnestad et al. |
| 8,657,790 B2 | 2/2014 | Tal et al. |
| 8,672,888 B2 | 3/2014 | Tal |
| 8,827,958 B2 | 9/2014 | Bierman et al. |
| 8,900,192 B2 | 12/2014 | Anderson et al. |
| 8,915,884 B2 | 12/2014 | Tal et al. |
| 8,956,327 B2 | 2/2015 | Bierman et al. |
| 9,375,553 B2 | 6/2016 | Chrisman |
| 9,402,979 B2 | 8/2016 | Mokaili et al. |
| 9,764,117 B2 | 9/2017 | Bierman et al. |
| 10,010,343 B2 | 7/2018 | Bierman et al. |
| 10,136,916 B2 | 11/2018 | Bierman et al. |
| 10,441,752 B2 | 10/2019 | Bierman et al. |
| 10,569,059 B2 | 2/2020 | Bierman |
| 11,027,099 B2* | 6/2021 | Bierman ............ A61M 39/0247 |
| 2002/0010436 A1 | 1/2002 | Becker et al. |
| 2002/0072712 A1 | 6/2002 | Nool et al. |
| 2002/0087076 A1 | 7/2002 | Meguro et al. |
| 2003/0032927 A1 | 2/2003 | Halseth et al. |
| 2003/0060842 A1 | 3/2003 | Chin et al. |
| 2003/0153874 A1* | 8/2003 | Tal .................... A61M 25/0606 |
| | | 604/164.1 |
| 2003/0171718 A1 | 9/2003 | Delegge |
| 2003/0199827 A1 | 10/2003 | Thorne |
| 2003/0216771 A1 | 11/2003 | Osypka et al. |
| 2004/0008191 A1 | 1/2004 | Poupyrev et al. |
| 2004/0092879 A1 | 5/2004 | Kraus et al. |
| 2004/0102789 A1 | 5/2004 | Baughman |
| 2004/0167439 A1 | 8/2004 | Sharrow |
| 2004/0171988 A1 | 9/2004 | Moretti |
| 2004/0193112 A1 | 9/2004 | Glazier et al. |
| 2004/0199197 A1 | 10/2004 | Eidenschink et al. |
| 2004/0239687 A1 | 12/2004 | Idesawa et al. |
| 2004/0267202 A1 | 12/2004 | Potter |
| 2005/0027263 A1 | 2/2005 | Woehr et al. |
| 2005/0090835 A1 | 4/2005 | Deal et al. |
| 2005/0113798 A1 | 5/2005 | Slater et al. |
| 2005/0143770 A1 | 6/2005 | Carter et al. |
| 2005/0245875 A1 | 11/2005 | Restelli et al. |

(56) References Cited

U.S. PATENT DOCUMENTS

| | | |
|---|---|---|
| 2006/0015039 A1 | 1/2006 | Cassidy et al. |
| 2006/0015071 A1 | 1/2006 | Fitzgerald |
| 2006/0149293 A1 | 7/2006 | King et al. |
| 2006/0274036 A1 | 12/2006 | Hoiki et al. |
| 2007/0021685 A1 | 1/2007 | Oepen et al. |
| 2007/0060889 A1 | 3/2007 | Adams |
| 2007/0112302 A1 | 5/2007 | Yu |
| 2007/0123825 A1 | 5/2007 | King et al. |
| 2007/0161908 A1 | 7/2007 | Goldman et al. |
| 2007/0270751 A1 | 11/2007 | Stangenes et al. |
| 2007/0282300 A1 | 12/2007 | Allawia et al. |
| 2008/0004569 A1 | 1/2008 | McCrystle et al. |
| 2008/0097386 A1 | 4/2008 | Osypka |
| 2008/0234728 A1 | 9/2008 | Starkksen |
| 2008/0294111 A1 | 11/2008 | Tal et al. |
| 2009/0018508 A1 | 1/2009 | Fisher et al. |
| 2009/0036843 A1 | 2/2009 | Erskine |
| 2009/0143737 A1 | 6/2009 | Kobayashi et al. |
| 2009/0149857 A1 | 6/2009 | Culbert et al. |
| 2009/0163861 A1 | 6/2009 | Carlyon |
| 2009/0177163 A1 | 7/2009 | King et al. |
| 2009/0221961 A1 | 9/2009 | Tal et al. |
| 2009/0227843 A1 | 9/2009 | Smith et al. |
| 2009/0259186 A1 | 10/2009 | Smith et al. |
| 2009/0264867 A1 | 10/2009 | Schweikert et al. |
| 2009/0312786 A1 | 12/2009 | Trask et al. |
| 2010/0042049 A1 | 2/2010 | Leeflang et al. |
| 2010/0069880 A1 | 3/2010 | Grayzel et al. |
| 2010/0191189 A1 | 7/2010 | Harding et al. |
| 2010/0256567 A1 | 10/2010 | Smith |
| 2011/0021994 A1 | 1/2011 | Anderson et al. |
| 2011/0046564 A1 | 2/2011 | Zhong |
| 2011/0202006 A1 | 8/2011 | Bierman et al. |
| 2011/0218496 A1 | 9/2011 | Bierman |
| 2011/0276002 A1 | 11/2011 | Bierman |
| 2012/0004665 A1 | 1/2012 | Defossez et al. |
| 2012/0130307 A1 | 5/2012 | Pobitschka |
| 2012/0136308 A1 | 5/2012 | Racz |
| 2012/0179144 A1 | 7/2012 | Carleo |
| 2012/0283640 A1 | 11/2012 | Bierman et al. |
| 2014/0025036 A1 | 1/2014 | Bierman et al. |
| 2014/0081210 A1 | 3/2014 | Bierman et al. |
| 2014/0207069 A1 | 7/2014 | Bierman et al. |
| 2014/0221977 A1 | 8/2014 | Belson |
| 2014/0276432 A1 | 9/2014 | Bierman et al. |
| 2015/0126930 A1 | 5/2015 | Bierman et al. |
| 2015/0297868 A1 | 10/2015 | Tal et al. |
| 2015/0351793 A1 | 12/2015 | Bierman et al. |
| 2017/0291009 A1 | 10/2017 | Sos |
| 2018/0001060 A1 | 1/2018 | Bierman et al. |
| 2019/0076166 A1 | 3/2019 | Bierman |

FOREIGN PATENT DOCUMENTS

| | | |
|---|---|---|
| DE | 8914941 U1 | 9/1990 |
| DE | 20211804 U1 | 1/2003 |
| EP | 0129745 A2 | 1/1985 |
| EP | 0139091 A1 | 5/1985 |
| EP | 0352928 A1 | 1/1990 |
| EP | 0411605 A1 | 2/1991 |
| EP | 0502714 A1 | 9/1992 |
| EP | 0583144 A1 | 2/1994 |
| EP | 0730880 A1 | 9/1996 |
| EP | 0734739 A2 | 10/1996 |
| EP | 0745409 A1 | 12/1996 |
| EP | 0750916 A2 | 1/1997 |
| EP | 0806221 A2 | 11/1997 |
| EP | 0904023 B1 | 7/2004 |
| EP | 1570793 A2 | 9/2005 |
| FR | 2 368 968 A1 | 5/1978 |
| JP | 5351692 A | 5/1978 |
| JP | 04504809 A | 8/1992 |
| JP | 06285172 A | 10/1994 |
| JP | 07148270 A | 6/1995 |
| JP | 08336593 A | 12/1996 |
| JP | 11299897 A | 11/1999 |
| JP | 2001190682 A | 7/2001 |
| JP | 2002172174 A | 6/2002 |
| JP | 2003512903 A | 4/2003 |
| JP | 2003154013 A | 5/2003 |
| JP | 2004500218 A | 1/2004 |
| JP | 2004097843 A | 4/2004 |
| JP | 2005514114 A | 5/2005 |
| JP | 2007503172 A | 2/2007 |
| JP | 2007209721 A | 8/2007 |
| JP | 2010504295 A | 2/2010 |
| JP | 2010510039 A | 4/2010 |
| JP | 2014526930 A | 10/2014 |
| JP | 2016163667 A | 9/2016 |
| KR | 1020050027359 A | 3/2005 |
| WO | 8301575 A1 | 5/1983 |
| WO | 8807388 A1 | 10/1988 |
| WO | 9218193 A1 | 10/1992 |
| WO | 9311812 A1 | 6/1993 |
| WO | 9312826 A1 | 7/1993 |
| WO | 9412233 A1 | 6/1994 |
| WO | 9804189 A1 | 2/1998 |
| WO | 9824494 A1 | 6/1998 |
| WO | 9857685 A1 | 12/1998 |
| WO | 0000104 A1 | 1/2000 |
| WO | 0123028 A1 | 4/2001 |
| WO | 0124865 A1 | 4/2001 |
| WO | 0141860 A1 | 6/2001 |
| WO | 0178595 A1 | 10/2001 |
| WO | 2003041598 A1 | 5/2003 |
| WO | 03057272 A2 | 7/2003 |
| WO | 2004000407 A1 | 12/2003 |
| WO | 2006119503 A1 | 11/2006 |
| WO | 2008064332 A2 | 5/2008 |
| WO | 2011162866 A1 | 12/2011 |
| WO | 2012117028 A2 | 9/2012 |
| WO | 2013067518 A1 | 5/2013 |
| WO | 2019168864 A1 | 9/2019 |

OTHER PUBLICATIONS

International Search Report and Written Opinion in Application No. PCT/US2019/019640 dated Jun. 5, 2019 31 pages.

U.S. Department of Health and Human Resources, "Medical Devices with Sharps Injury Prevention Features," Guidance for Industry and FDA Staff in 20 pages. Issued on Aug. 9, 2005.

Arrow International, Inc., "Arrow Trauma Products", TRM-C 12/00 11 M, 2000, 12 pages.

International Search Report and Written Opinion in Application No. PCT/US2016/027972, dated Jul. 15, 2016 in 15 pages.

International Preliminary Report on Patentability in Application No. PCT/US2016/027972, dated Oct. 31, 2017 in 7 pages.

Photos of a peripheral emergency infusion device Applicant believes to be produced by Arrow International Inc., Jul. 20, 2011, 6 pages.

Photos of a splittable catheter design, Jul. 20, 2011, 3 pages.

Photos of an infusion device Applicant believes to be produced by B. Braun Medical Inc., Jul. 20, 2011, 6 pages.

Extended European Search Report dated Sep. 8, 2021 for European Application No. 21172362.2, 8 pages.

* cited by examiner

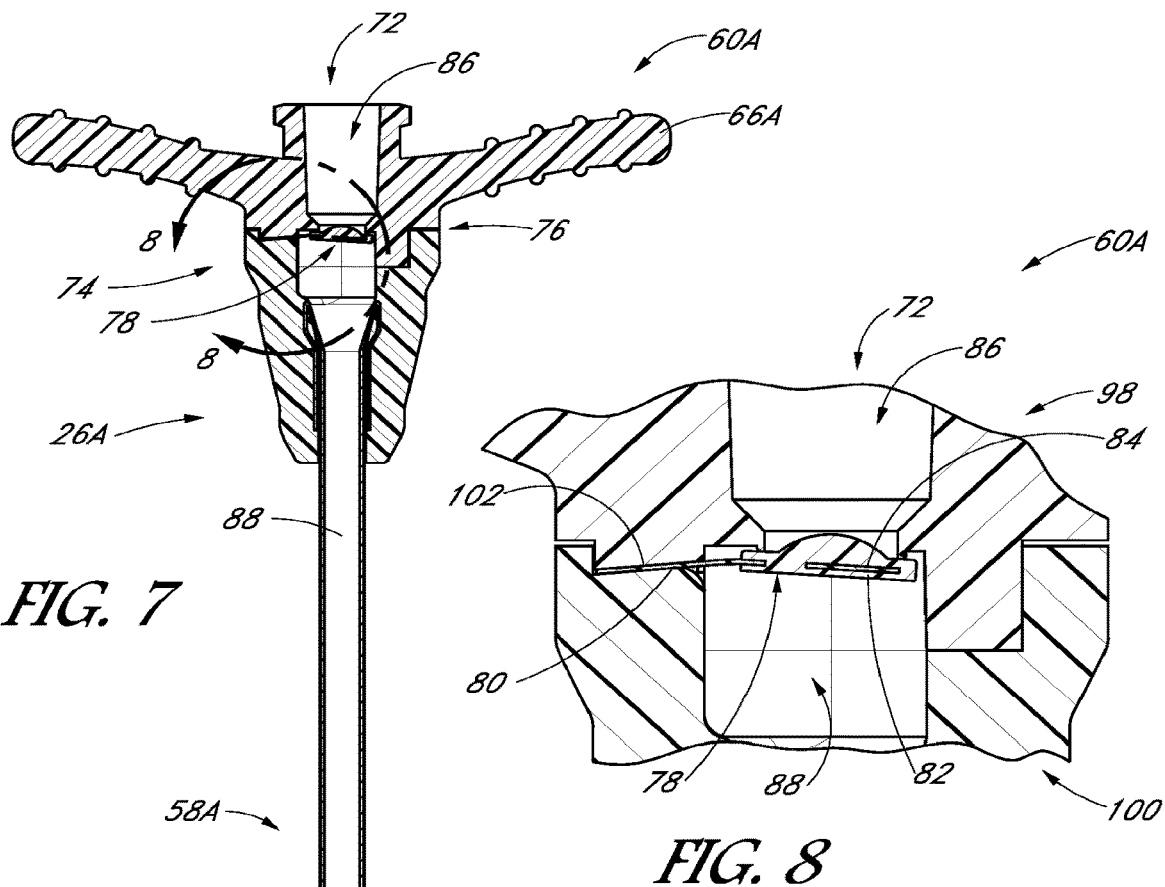
FIG. 7
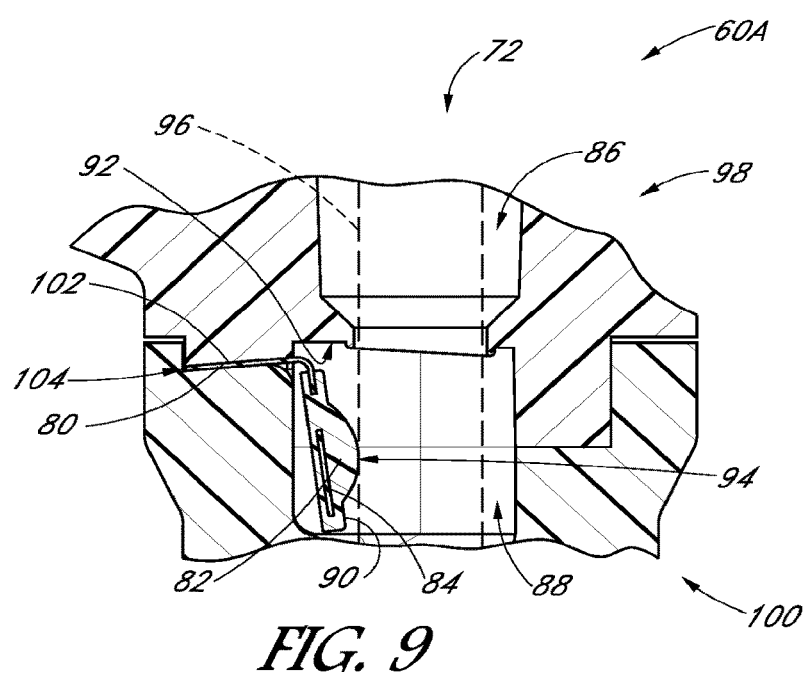
FIG. 8
FIG. 9

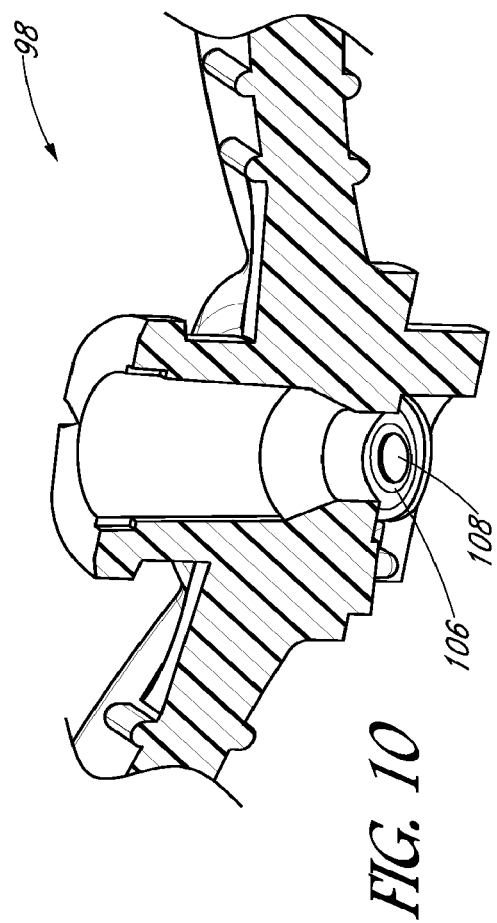
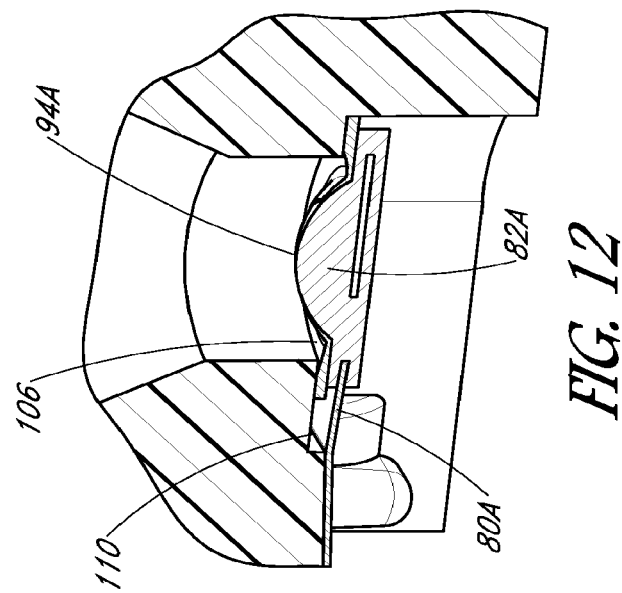
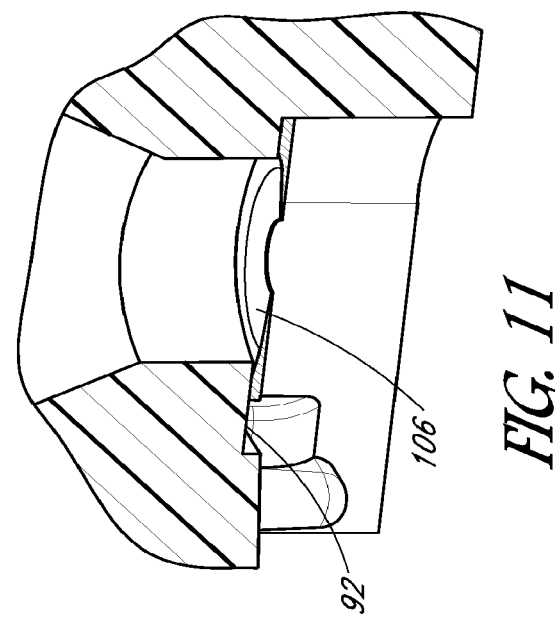
FIG. 10
FIG. 11
FIG. 12

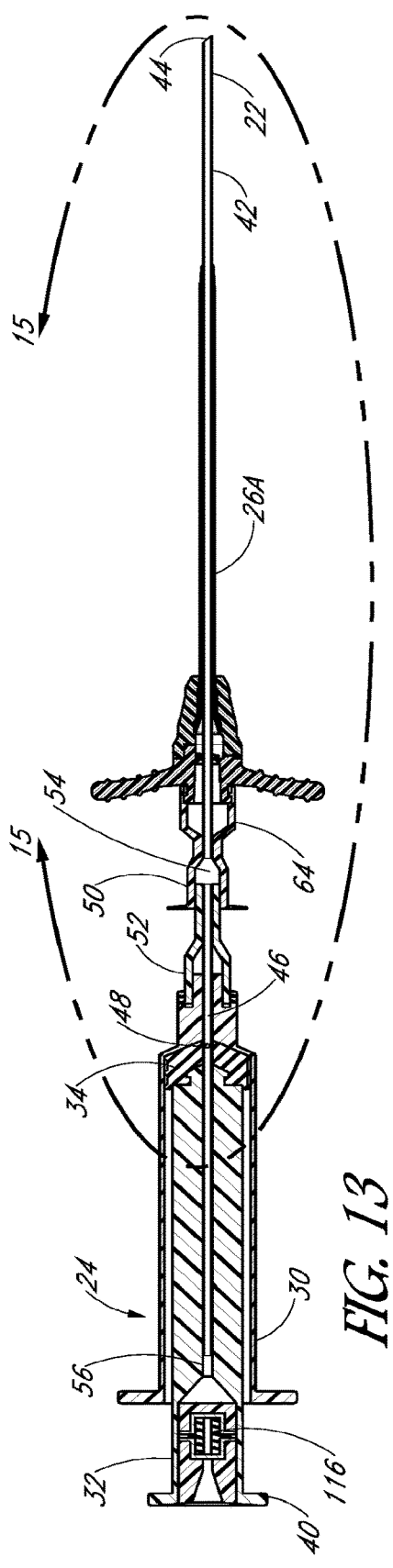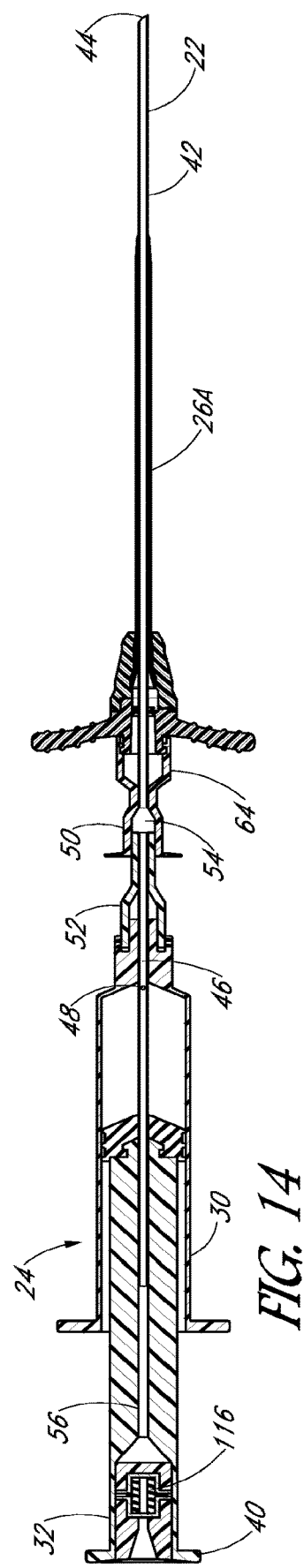

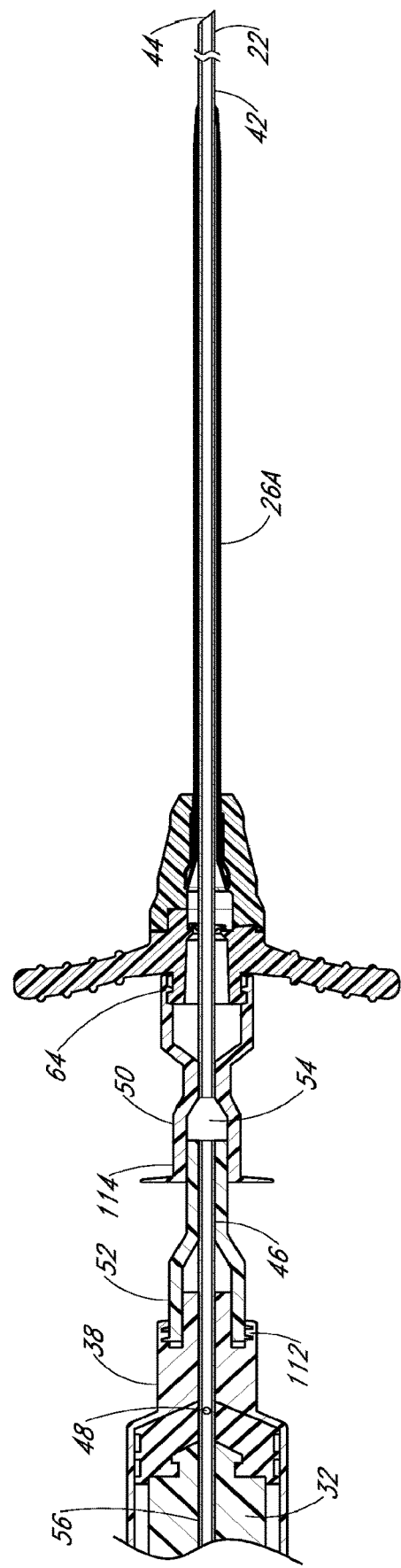

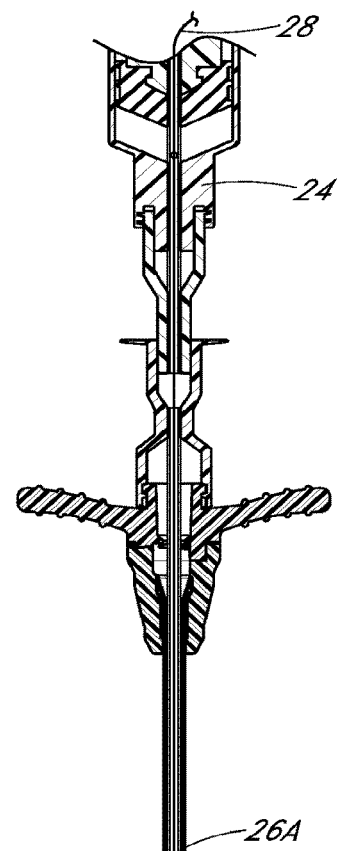
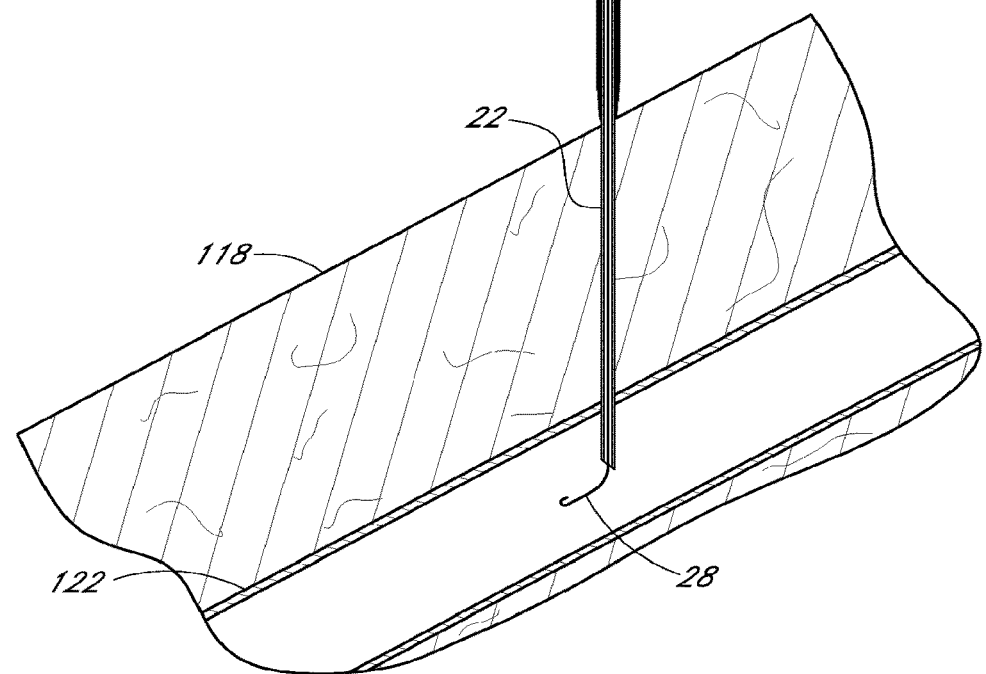
FIG. 18A

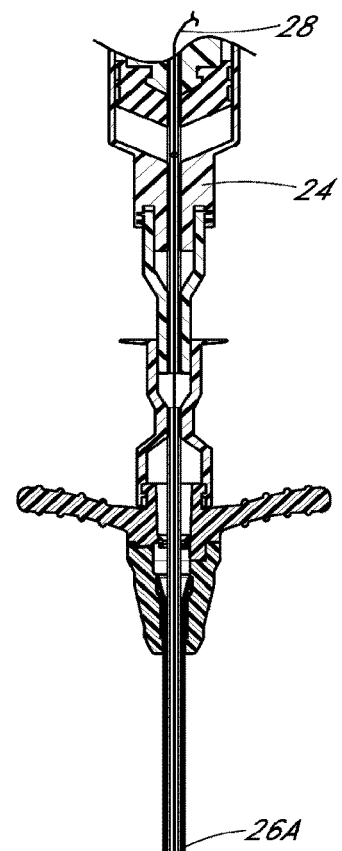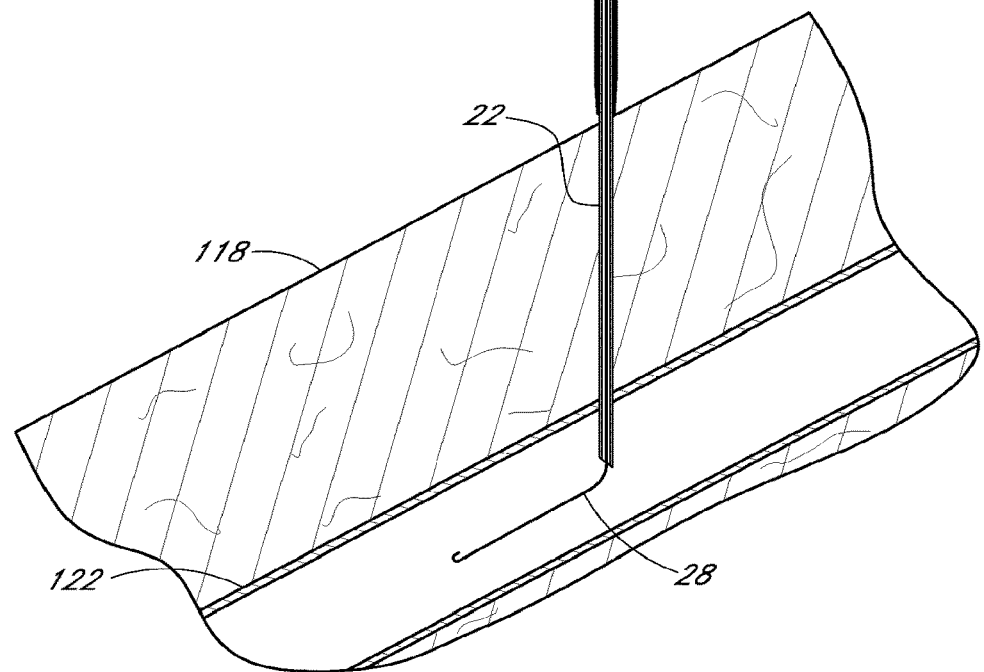
FIG. 18B

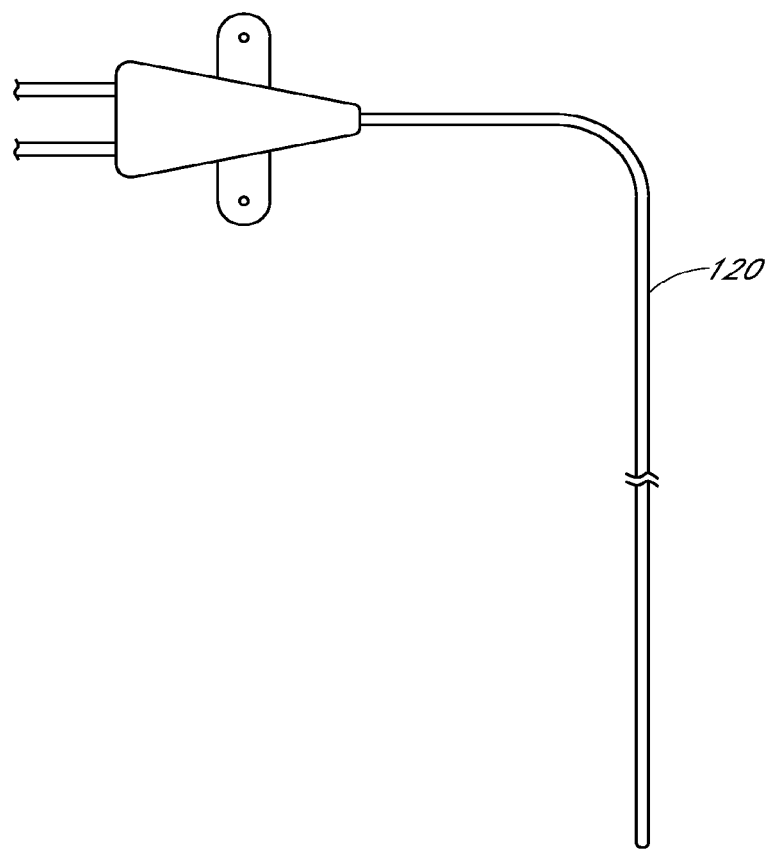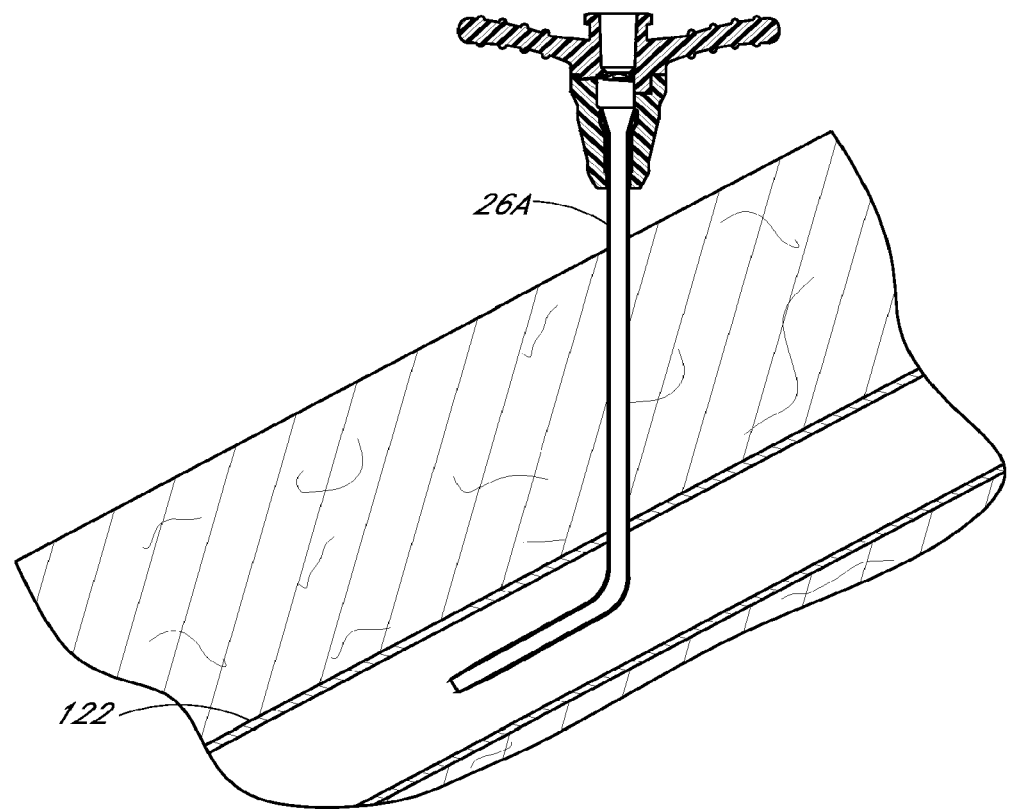
FIG. 21

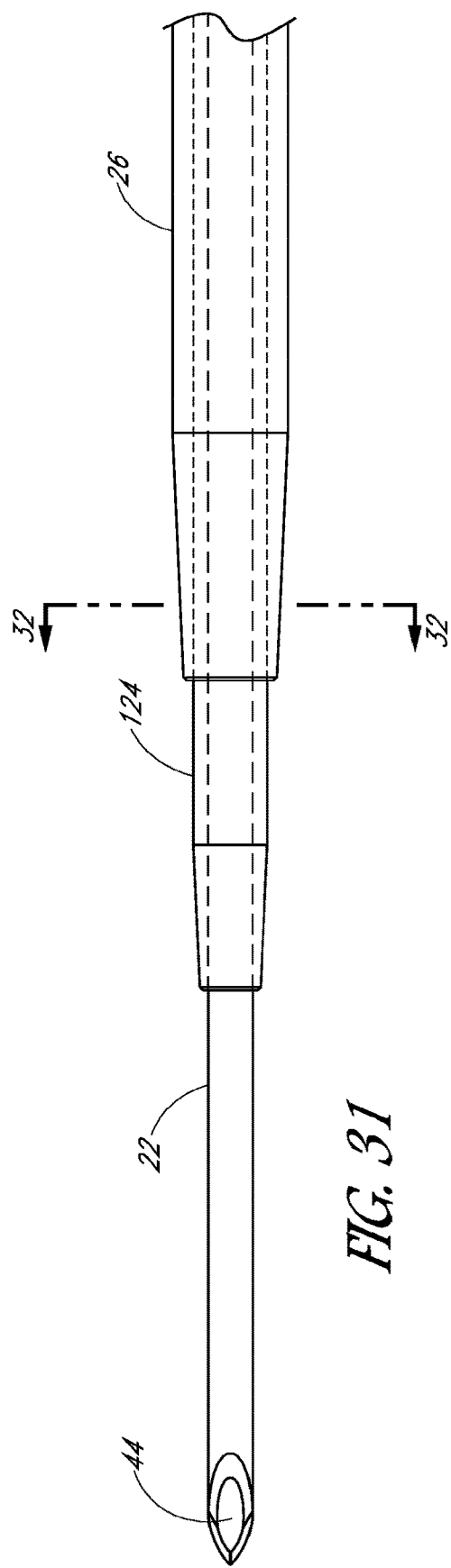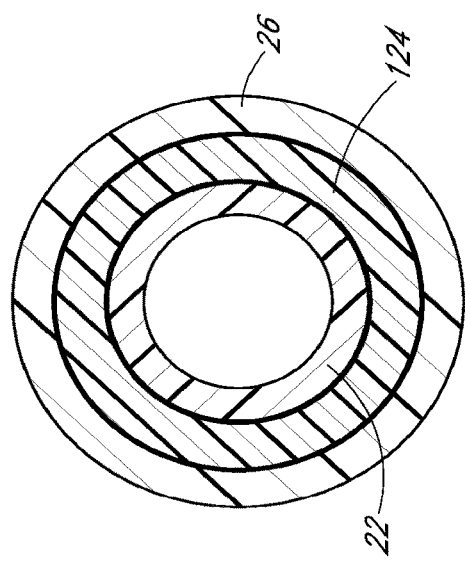
FIG. 31
FIG. 32

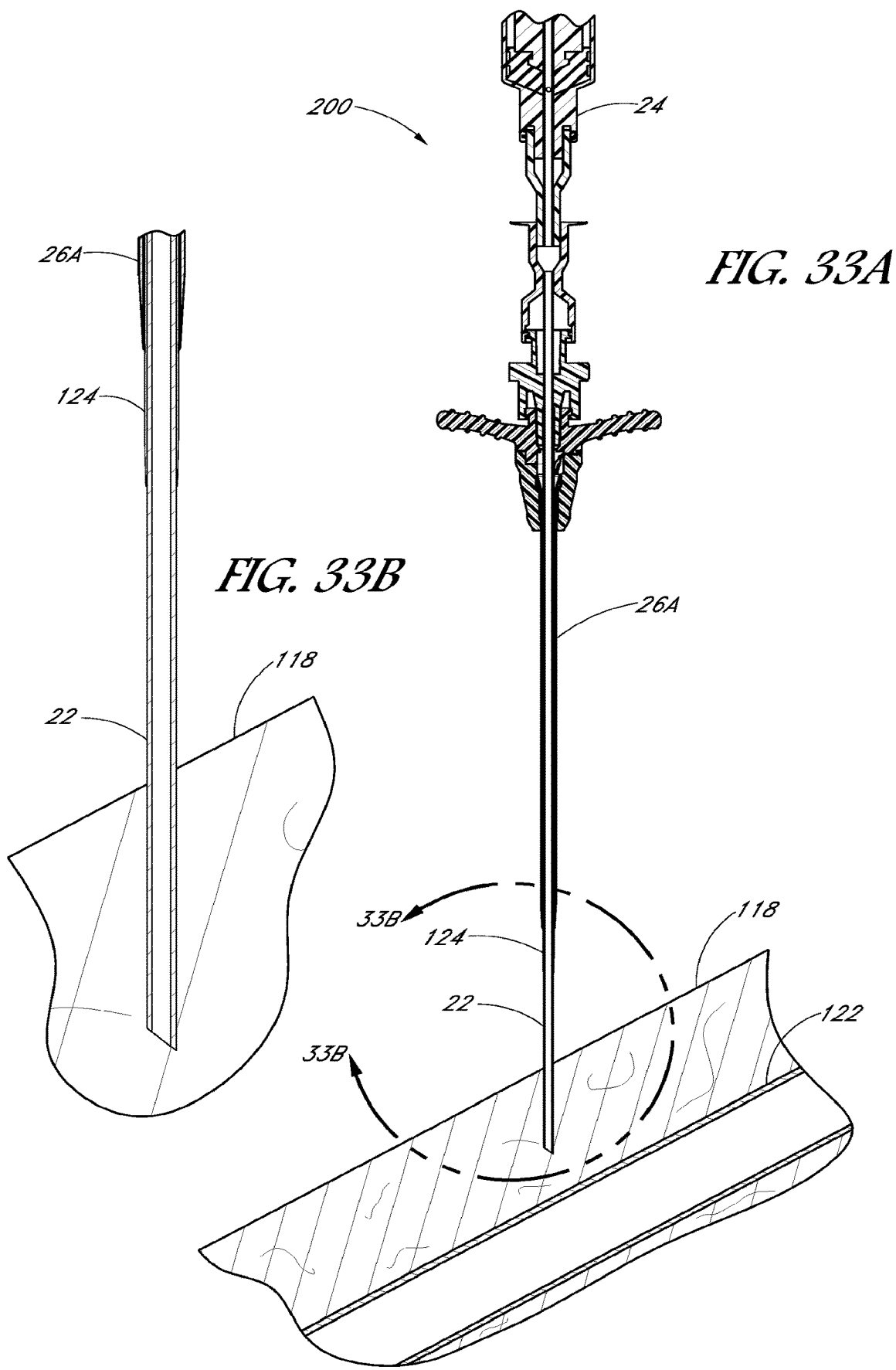

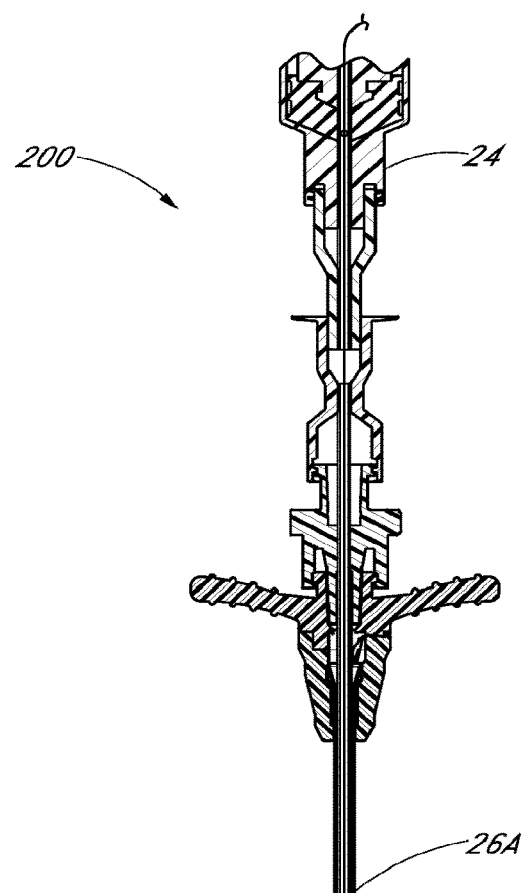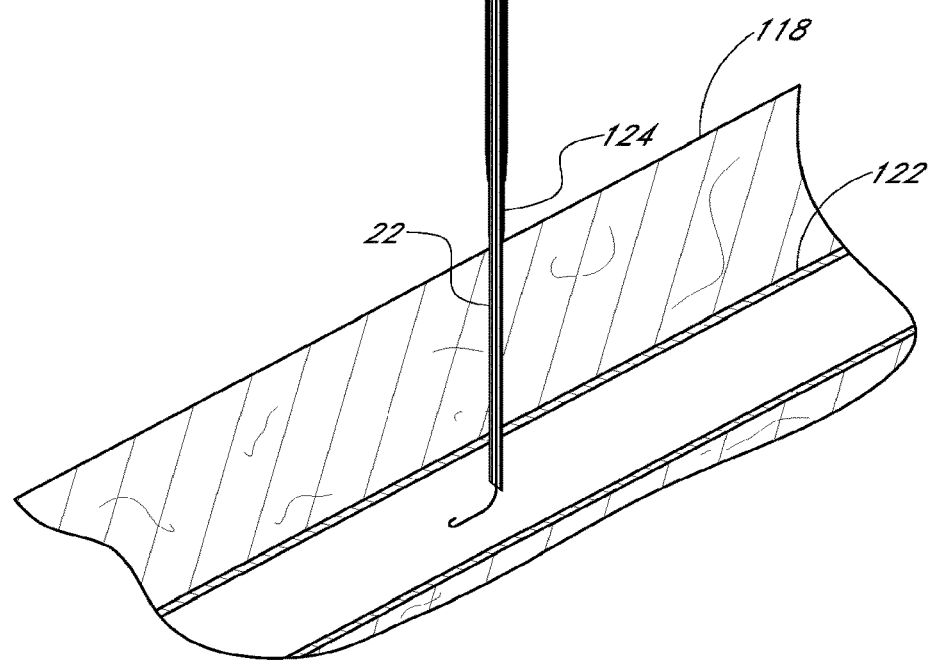
FIG. 35A

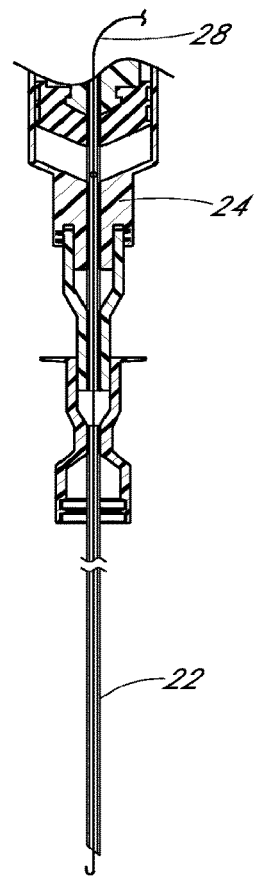
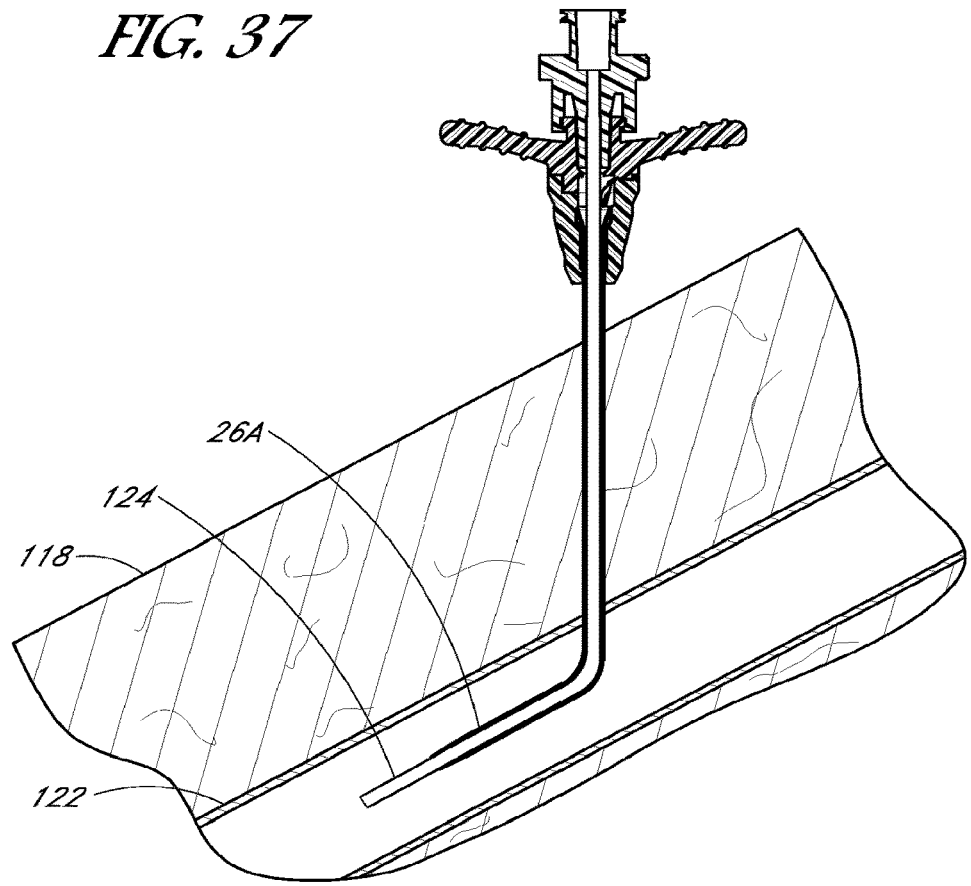
FIG. 37

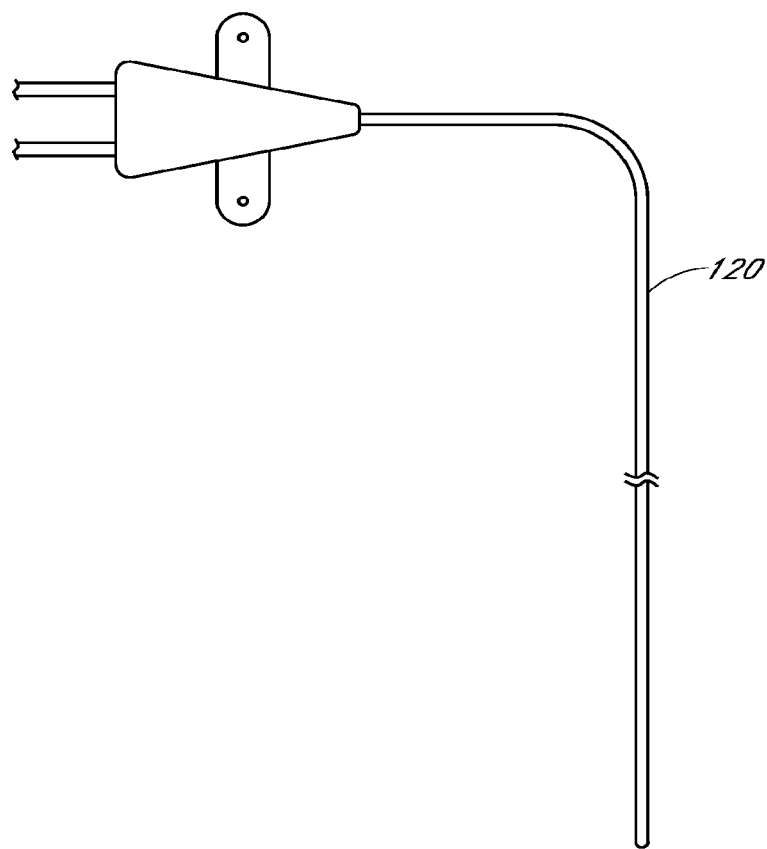
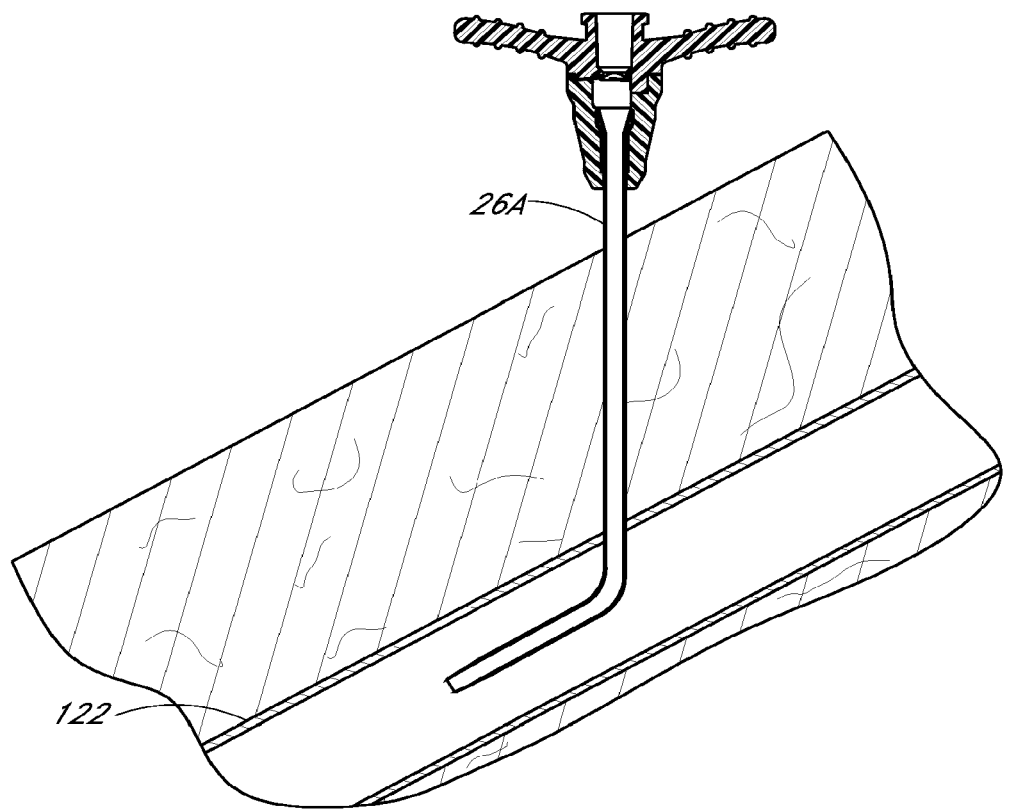
FIG. 39

VASCULAR ACCESS DEVICE

CROSS-REFERENCE TO RELATED APPLICATIONS

The present application claims the benefit of priority under 35 U.S.C. § 120 as a continuation from U.S. patent application Ser. No. 15/568,765 entitled "VASCULAR ACCESS DEVICE," filed on Oct. 23, 2017, which is the U.S. National Stage Entry of PCT International Patent Application No. PCT/US2016/027972 entitled "VASCULAR ACCESS DEVICE," filed on Apr. 15, 2016, which claims the benefit of priority to U.S. Provisional Pat App. 62/155,368 entitled "VASCULAR ACCESS DEVICE," filed on Apr. 30, 2015, and to U.S. Provisional Pat. App. 62/209,841 entitled "VASCULAR ACCESS DEVICE," filed on Aug. 25, 2015, the disclosures of which are all hereby incorporated by reference in their entireties.

BACKGROUND

Field

The present disclosure is generally directed to access devices for introducing and/or delivering a medical article (such as, for example, a catheter, cannula, sheath, etc.) into a body space, such as, for example, an artery, vein, vessel, body cavity, or drainage site, and more specifically, to a distal tip section of such devices.

Description of the Related Art

Various medical devices, for example, catheters, cannulas, sheaths, etc., are often introduced into a patient, for example, in an artery, vein, body cavity, or drainage site, to deliver fluids to or withdraw fluids from the patient. For example, a catheter or vascular sheath can be introduced into a patient's blood vessel using a Raulerson technique. This technique involves inserting an introducer needle attached to a Raulerson syringe into the patient's blood vessel and then inserting a guide wire through the rear of the syringe plunger and into the vessel. The Raulerson syringe and needle are removed leaving the guide wire extending into the patient A skin-nick may be performed adjacent to the guide wire to enlarge the puncture site. A catheter or other medical article can be threaded over the guide wire and into the patient Once the catheter is in a desired location, the guide wire is removed.

The above technique requires exchanges over the guide wire, which presents the risk of losing cannulation, lost guide wire, and contamination. Further, during the skin-nick step the guide wire may be severed due to the guide wire being exposed. The overall technique is time intensive risking movement of the medical article(s) and guide wire relative to the patient.

SUMMARY

The access devices described herein advantageously provide improved mechanisms for confirming vascular access and achieving medical device placement within the vasculature.

In some embodiments, an access device for placing a medical article within a body space includes a syringe, a needle, and a sheath coaxially disposed about the needle. In certain embodiments, the access device further includes a dilator disposed coaxially about the needle and within the sheath. The syringe includes a hollow barrel having a plunger slideably disposed therein. The syringe functions as a standard airtight syringe as well as a device which provides a passageway for a guide wire into a patient's vasculature.

The plunger comprises a central channel and valve element disposed in the central channel. A normally closed centrally disposed slit or aperture is formed in the center of the valve element.

The hollow barrel supports a needle affixed to the tip thereof. The needle includes an exterior portion extending outwardly from the tip of the hollow barrel. The needle further includes an interior portion having an aperture formed therethrough adjacent to the tip of the hollow barrel. The interior portion extends into the interior of the hollow barrel such that at least a portion of the interior portion is at least partially disposed within the centrally disposed channel in the plunger during use.

Disposed concentrically around the exterior portion of the needle is a sheath. The sheath releasably secures to the syringe to allow the sheath to be slid in a distal direction over the exterior portion of the needle and into the patient. Once the syringe is removed leaving the sheath, a catheter may be inserted through the sheath and into the patient. The sheath may be pealable so as to allow the sheath to be removed from around an inserted catheter and from the patient.

In certain embodiments, a dilator is disposed concentrically around the exterior portion of the needle and within the sheath. A distal end of the dilator extends beyond a distal end of the sheath. The dilator can releasably secure to one or both of the syringe and the sheath. Being releasably secured to the syringe allows the dilator to be slid in concert with the sheath in a distal direction over the exterior portion of the needle and into the patient. Once the distal ends of the dilator and sheath are disposed within the patient and the syringe is removed, the dilator is disengaged from the sheath and then removed. Once the syringe and dilator are removed leaving the sheath, a catheter may be inserted through the sheath and into the patient. The sheath may be pealable so as to allow the sheath to be removed from around an inserted catheter and from the patient.

In use the vascular access device is aspirated by the retraction of the plunger permitting fluid to pass into the interior of the syringe barrel through the aperture formed on the interior needle portion. During this aspiration, air is prevented from entering the valve chamber by the valve element.

Then a guide wire may be passed through the central channel of the plunger and the interior and exterior portions of the needle to reach the blood vessel. The guide wire passes through the valve element to form a seal therewith to prevent either liquid or air from passing through the valve element during the introduction of the guide wire into the patient.

The sheath is then slid over the exterior portion of the needle and guide wire and into the vasculature of the patient. The syringe and the guide wire are removed from the patient leaving the sheath. In certain embodiments, the sheath comprises a valve element for preventing liquid from flowing through the sheath.

In embodiments which include a dilator, the dilator is initially releasably secured to the syringe with the sheath being releasably secured to the dilator. Releasably securing the dilator to the sheath ensures the distal end of the dilator extends beyond the distal end of the sheath during their insertion into the vasculature. The dilator is then disengaged from the syringe while still being engaged with the sheath. Together, the dilator and sheath are then slid over the exterior portion of the needle and guide wire and into the vasculature of the patient The syringe and guide wire are then removed from the patient leaving the dilator and the sheath. The dilator is disengaged from the sheath and slid in a proximal direction out of the sheath. In certain embodiments, the syringe, guide wire, and dilator and removed from the sheath at the same time. In certain embodiments, the sheath comprises a valve element for preventing liquid from flowing through the sheath.

In some embodiments, the sheath includes a sheath body, a hub, and a valve. The valve may include an annular member and a sealing member. The sheath body includes a generally flexible tubular structure, a proximal end, and a distal end and defines a longitudinal axis. The hub is coupled with the proximal end of the sheath body, and the sheath body and hub have aligned openings forming a passage therethrough. The annular member of the valve is disposed against a surface of the hub facing the sheath body and includes an opening therethrough. The sealing member of the valve has an engagement portion coupled with a structure of the sheath assembly disposed generally between the surface of the hub and the distal end of the sheath body. The sealing member also has a seal portion projecting into sealing engagement with the opening in the annular member in a sealing position and disposed away from the opening in the annular member in an open position.

In some embodiments, the access device for placing a medical article within a body space includes a barrel and a plunger slidingly disposed in the barrel. The plunger has a channel sized and shaped to receive a guide wire therethrough. The barrel defines a fluid chamber. The access device further includes an interior needle portion at least partially disposed in the channel. The interior needle portion includes an aperture through a side wall of the interior needle portion and into the fluid chamber. The access device further includes an exterior needle portion extending from the barrel and in flow communication with the interior needle portion and the fluid chamber. The access device further includes a sheath coaxially disposed about the exterior needle portion and slideable along the exterior needle portion. A distal end of the sheath is positioned proximal to a distal end of the exterior needle portion.

In some embodiments, the access device for placing a medical article within a body space includes a syringe and a needle extending from the syringe. The syringe has a channel configured to receive a guide wire extending through the needle. The access device further includes a sheath coaxially disposed about the needle and slidable along the needle.

In some embodiments, a method for placing a medical article within a body space includes the steps of penetrating a blood vessel with an access device. The access device includes a syringe, a needle extending from the syringe, and a sheath coaxially disposed about the syringe. The syringe has a channel in flow communication with the needle. The method further includes feeding a guide wire through the channel, the needle, and into the blood vessel and sliding the sheath along the needle in a distal direction until at least a portion of the sheath is disposed in the blood vessel. The method further includes removing the syringe, the needle, and the guide wire from the blood vessel leaving the sheath.

In some embodiments, a dilator is employed between the exterior portion of the needle and the interior surface of the sheath to increase a size of the opening into the vasculature of the patient for the sheath.

BRIEF DESCRIPTION OF THE DRAWINGS

The foregoing and other features, aspects, and advantages of the embodiments of the invention are described in detail below with reference to the drawings of various embodiments, which are intended to illustrate and not to limit the embodiments of the invention. The drawings comprise the following figures in which:

FIG. 7 is a side cross-sectional view of the sheath of FIG. 5 taken at 7-7.

FIGS. 8 and 9 are enlarged views of a section of the sheath of FIG. 7 showing a valve element in a closed and opened position, respectively.

FIGS. 10, 11, and 12 are enlarged views of a section of an embodiment of a sheath that includes an annular member, a resilient plate, and sealing element.

FIG. 13 is a cross-section view of the syringe from FIG. 1 in combination with the valved sheath from FIG. 5 and shows a plunger of the syringe in an advanced state.

FIG. 14 is similar to FIG. 13 except the plunger of the syringe is in a retracted state.

FIG. 15 is an enlarged cross-section view from FIG. 13 taken at 15-15.

FIG. 18A is a cross-section view similar to FIG. 17 except a guide wire has been fed through the plunger and needle and into the vasculature of the patient.

FIG. 18B is a cross-section view similar to FIG. 18A except the guide wire has been extended further into the vasculature of the patient.

FIG. 21 is a cross-section view similar to FIG. 20 except a catheter is aligned with the sheath for insertion into the patient's vasculature.

FIG. 31 is an enlarged view of a portion of the embodiment depicted in FIG. 30 and illustrates portions of the needle, dilator, and sheath.

FIG. 32 is an enlarged cross-sectional view of the embodiment depicted in FIG. 31 taken at a longitudinal location wherein the needle, dilator, and sheath overlap along line 32-32.

FIG. 33A is a cross-section view of the access device illustrated in FIG. 28 penetrating a body.

FIG. 33B is an enlarged partial cross-section view from FIG. 33A of a distal end of the needle.

FIG. 35A is a cross-section view similar to FIG. 34A except a guide wire has been fed through the plunger and needle and into the vasculature of the patient.

FIG. 37 is a cross-section view similar to FIG. 36 except the syringe and the guide wire have been removed from the patient leaving the dilator and the sheath in the vasculature.

FIG. 39 is a cross-section view similar to FIG. 38 except a catheter is aligned with the sheath for insertion into the patient's vasculature.

DETAILED DESCRIPTION

Figure 1:
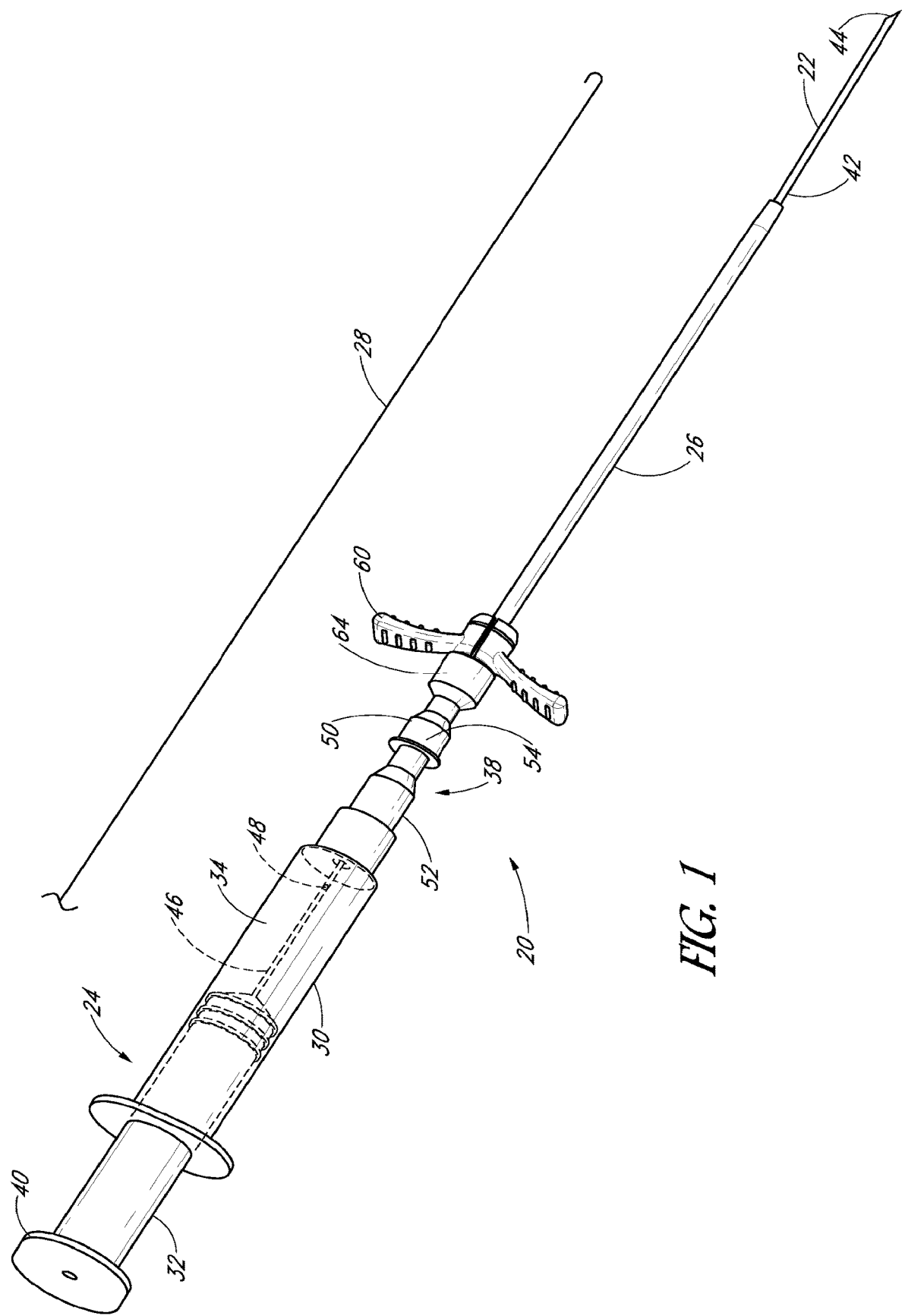
FIG. 1 is a perspective view of an embodiment of an access device having a syringe with a needle coaxially aligned with a medical article such as a sheath. A guide wire for use with the access device is also shown.
Figure 2:
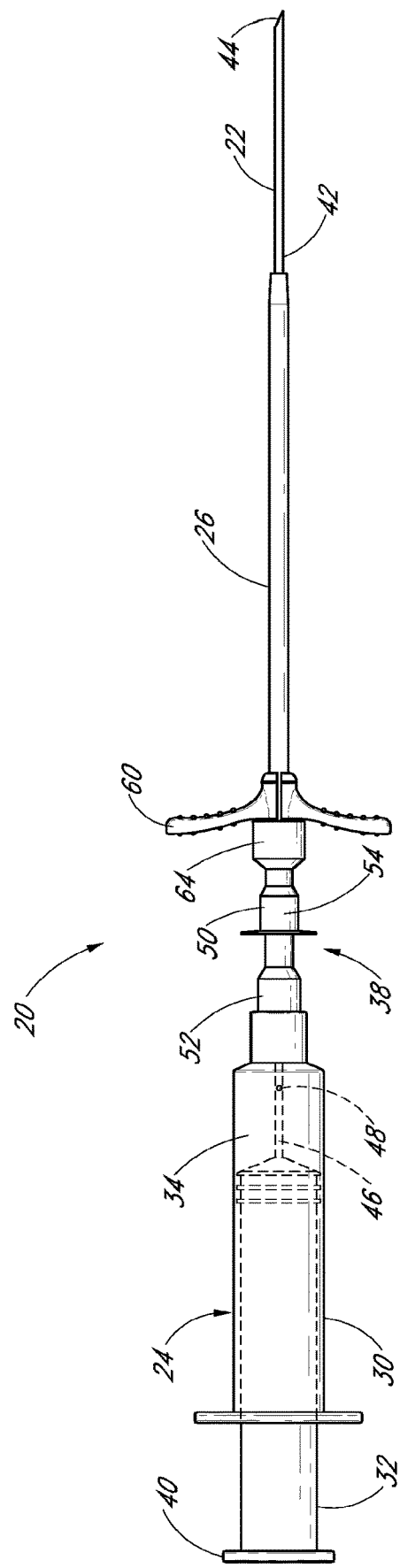
FIG. 2 is a plan view of the embodiment depicted in FIG. 1 without the guide wire.
Figure 24:
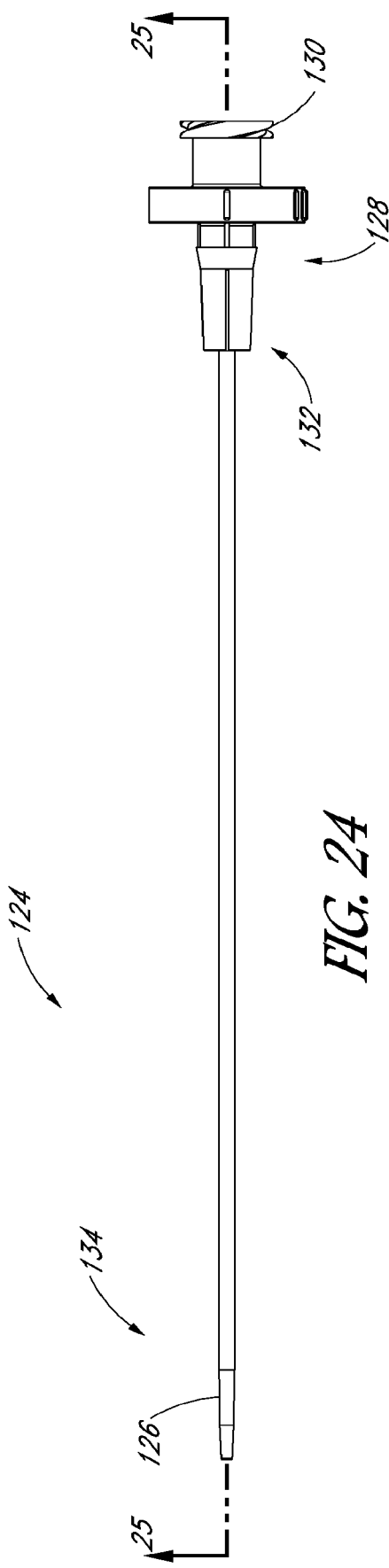
FIG. 24 is a plan view of a dilator that can be used with the access device of FIG. 1.
Figure 25:
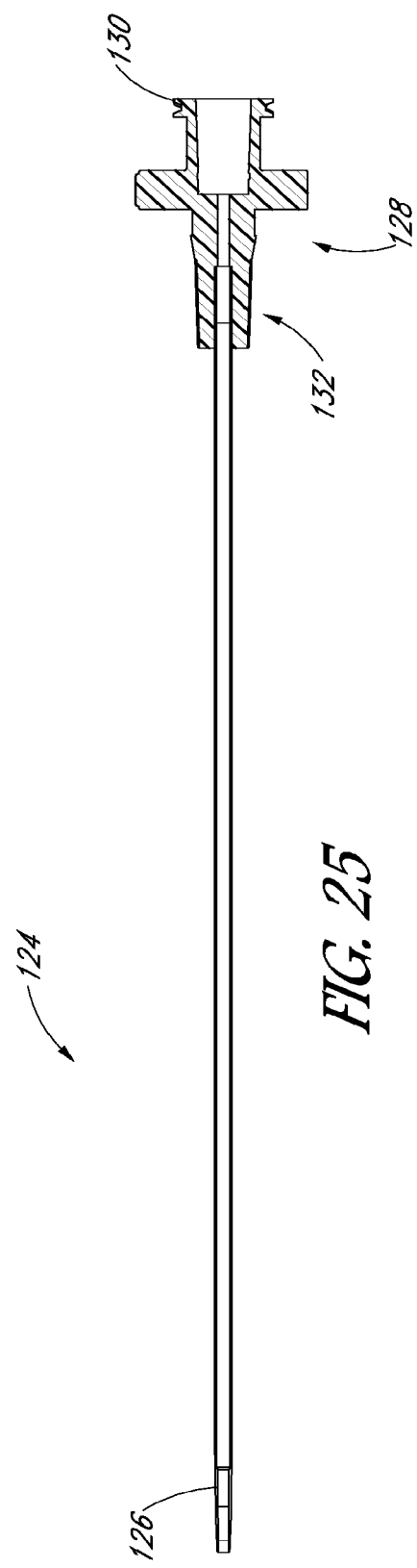
FIG. 25 is a cross-sectional view taken along the lines 25-25 in FIG. 24.

In various circumstances a physician may wish to introduce a catheter or sheath into a space within a patient's body, for example, a blood vessel or drainage site, to introduce fluids to the space or remove fluids from the space. Various access devices are known in the art. Examples of an improved access device are described in U.S. patent application Ser. No. 14/238,832, entitled "ACCESS DEVICE WITH VALVE," filed Feb. 13, 2014, published as US 2014/0207069 on Jul. 24, 2014, the entire contents of which is incorporated by reference herein. FIGS. 1 and 2 illustrate an embodiment of an access device 20 that can be used, for example, in performing a modified Raulerson technique to introduce a catheter or sheath into a patient's blood vessel. Certain embodiments of the access device 20 may further include a dilator 124 as is illustrated in FIGS. 24 and 25. An embodiment of the access device that includes the dilator 124 is illustrated in FIGS. 26 through 41.

While the access devices 20 described herein in the context of vascular access, the access device also can be used to access and place a medical article (e.g., catheter or sheath) into other locations within a patient's body (e.g., a drainage site) and for other purposes (e.g, for draining an abscess).

The present embodiment of the access device is disclosed in the context of placing an exemplary single-piece, tubular medical article into a body space within a patient. Once placed, the tubular article can then be used to receive other medical articles (e.g., catheters, guide wires, etc.) to provide access into the body space and/or be used to provide a passage way for introducing fluids into the body space or removing (e.g., draining) fluids from the body space. In the illustrated embodiment, the tubular medical article is a sheath or catheter that is configured primarily to provide a fluid passage into a vein. The principles of the present invention, however, are not limited to the placement of single piece sheaths or catheters, or to the subsequent insertion of a medical article via the sheath or catheter. Instead, it will be understood in light of the present disclosure that the access device disclosed herein also can be successfully utilized in connection with placing one or more other types of medical articles, including other types of sheaths, fluid drainage and delivery tubes, and single or multi-lumen catheters directly in the patient or indirectly via another medical article.

For example, but without limitation, the access devices disclosed herein can also be configured to directly or indirectly place central venous catheters, peripherally inserted central catheters, hemodialysis catheters, surgical drainage tubes, tear-away sheaths, multi-piece sheaths, PICC lines, IV lines, scopes, as well as electrical conduit for wires or cables connected to external or implanted electronic devices or sensors. As explained above, the medical articles listed above may be placed within the patient via a medical article that was placed within the patient via the access device.

Further, the embodiments disclosed herein are not limited to co-axial insertion of a single medical article. For example, two catheters may be inserted in the patient via an inserted sheath or a second catheter may be inserted in the patient via an inserted first catheter. Further, in addition to providing a conduit into the vessel or other body space, the medical article inserted via the access device can form a lumen that is in addition to the lumen(s) of the subsequently inserted medical article. One skilled in the art can also find additional applications for the devices and systems disclosed herein. Thus, the illustration and description of the access device in connection with a sheath (e.g., for micro puncture applications) is merely exemplary of one possible application of the access device.

FIG. 1 is a perspective view of an embodiment of an access device 20 having a syringe 24 with a needle 22 coaxially aligned with a medical article such as a sheath 26. A guide wire 28 for use with the access device is also shown. FIG. 2 is a plan view of the embodiment depicted in FIG. 1. With reference to FIGS. 1 and 2, an example embodiment of the access device 20 includes the needle 22, the syringe 24, and the tubular sheath 26. In the illustrated embodiment, the access device 20 also includes the guide wire 28. The sheath 26 can be coaxially disposed about the needle 22. The access device 20 allows the introduction of the guide wire 28 and subsequently the sheath 26 into a patient's body.

The syringe 24 comprises a syringe barrel 30 and a substantially cylindrical plunger 32 slideably disposed therein. As described more fully hereinafter, the access device 20 is capable of functioning as a standard air tight syringe as well as a device to introduce a catheter or guide wire 28 into the patient's body.

The barrel 30 comprises a hollow substantially cylindrical body having a hollow barrel tip 38 to support the needle 22 and a finger grasping element 40 formed on opposite ends thereof. The needle 22 comprises a first or exterior needle portion 42 including a piercing point 44 extending outwardly generally from the hollow barrel tip 38. The needle 22 further includes a second or interior needle portion 46 extending inwardly from the barrel tip 38 into the interior of the hollow substantially cylindrical syringe barrel 30. An aperture 48 is formed through the second portion 46 near a bottom of a fluid chamber 34. The aperture 48 extends, or provides a path, through the wall or side of the second needle portion 46. The aperture 48 can allow fora fluid, such as blood, to flow into the fluid chamber 34 during use of the access device 20. Blood flow into the fluid chamber 34 indicates to the physician or healthcare provider that the piercing point 44 of the exterior needle portion 42 has punctured a blood vessel. The aperture 48 can have a variety of shapes and orientations on the second needle portion 46. For example, the aperture 48 illustrated in FIG. 15 has a round shape. However, the shape of the aperture 48 is not limited to the illustrated embodiment and may be oblong square, or another shape.

The hollow barrel tip 38 comprises a first barrel tip section or needle hub 50 and a second barrel tip section 52 operatively receiving and supporting the first and second portions 42 and 46, respectively. An intermediate channel 54 is cooperatively formed between the first and second barrel tip sections 50 and 52 in coaxial alignment with the first or exterior needle portion 42 and second or interior needle portion 46. When the plunger 32 is fully advanced within the syringe barrel 30, the major portion of the second or interior portion 46 is disposed within a centrally disposed channel 56 in the plunger 32.

The sheath 26 includes a generally flexible tubular structure, a proximal end or hub 60, and a distal end or body 58, and defines a lumen along a longitudinal axis. The sheath hub 60 is coupled with the proximal end of the sheath body 58 and has a passage therethrough. Certain embodiments of the sheath 26 further include a valve coupled with a distal face of the hub 60. For example, the valve could be in the form of a diaphragm. The diaphragm provides fluid communication between the lumen and the passage when open and has a proximal face configured to seal when closed. The diaphragm can be configured to seal against a device disposed in the passage, diaphragm and lumen of the sheath 26 and/or when there is no device disposed in the sheath 26. Certain embodiments of the sheath 26 are splittable as described in more detail below. Accordingly, embodiments of the sheath 26 component of the access device 20 may be splittable and or include a valve structure for sealing the lumen through the sheath 26.

Figures 3, 4:
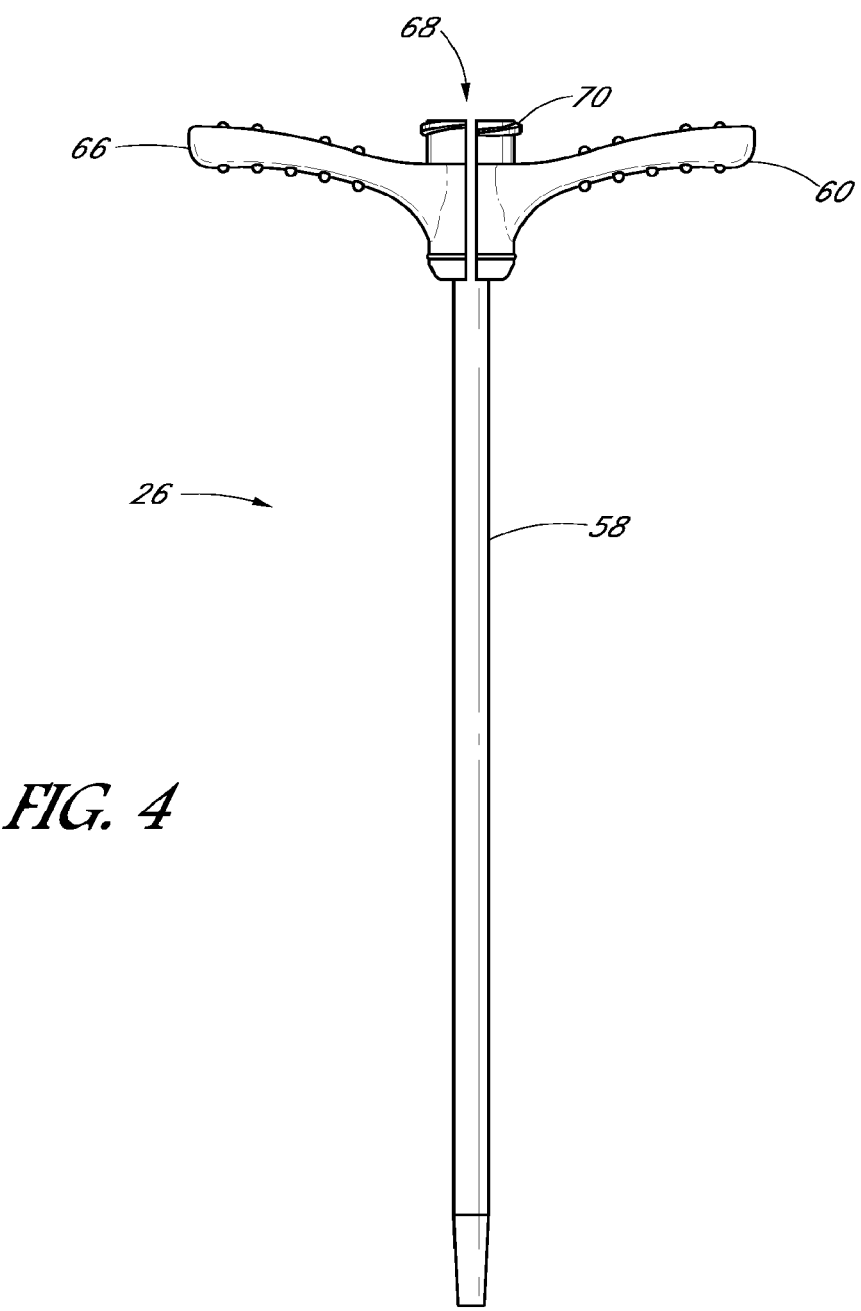
FIG. 3 is a proximal end view of the sheath from FIG. 1.
FIG. 4 is a plan view of the sheath of FIG. 3.

FIG. 3 is a proximal end view of the sheath 26 from FIG. 1. FIG. 4 is a plan view of the sheath 26 of FIG. 3. As shown in FIGS. 3 and 4, the sheath 26 includes a sheath body 58 and a sheath hub 60. In the embodiment illustrated in FIGS. 3 and 4, the sheath body 58 and/or sheath hub 60 can be optionally splittable along one or more split lines 68. A splittable sheath 26 provides the advantage of allowing a portion of or the entire sheath body 58 to be removed depending on the type of catheter or medical article that is to be inserted into the vessel after employing the access device 20. For example, after the catheter or other medical article is inserted into the vessel, a portion of the sheath body 58 can be separated or peeled-away and removed to reduce clutter at the access site. A peel-away sheath 26 can include perforations, serrations, skives, or other structures, or include other materials (e.g., PTFE with bismuth) to allow the physician or healthcare provider to remove easily a portion or the entire sheath body 58. In certain embodiments, the sheath 26 is not splittable.

The sheath hub 60 can include a locking structure 70 configured to engage, for example, a second locking structure 64 of the exterior needle portion 42. In certain embodiments which include a dilator, the locking structure 70 of the sheath hub 60 may secure to the dilator. The sheath body 58 may be a single piece sheath through which a catheter or other medical article is inserted into the vessel. In such an embodiment, the sheath body 58 forms a conduit for insertion of the catheter or other medical article. In addition to providing a conduit, the sheath 26 or a portion of the sheath 26 can form a lumen that is in addition to the lumen(s) of the catheter. For example, an equivalent to a triple lumen catheter can be formed by inserting a dual lumen catheter through the sheath body 58 with the sheath body 58 itself forming a third lumen. The sheath body 58 can be manufactured from a clear or at least somewhat transparent material to allow the physician or healthcare provider to see blood flowing through the sheath body 58.

In some such embodiments, the sheath hub 60 may comprise radially extending wings, handle structures, or tabs 66 to allow for easy release and removal of the sheath body 58 from other parts of the access device 20. Tabs 66 can have any of a number of different shapes and/or surface features to facilitate them being gripped, and are not limited to the substantially T-shape shown. Tabs 66 are separable, to allow the splittable sheath 26 to separate along one or more split lines, such as a predetermined split or separation line 68 The split line 68 can extend through either or both the sheath hub 60 and the sheath body 58. The split line(s) 68 can extend generally parallel to one or more longitudinal axes defined by the sheath body 58 and/or sheath hub 60, but in some embodiments, the split line(s) 68 can extend substantially non-parallel. As illustrated most clearly in FIG. 23, splitting the sheath 26 along the split line 68 can separate the sheath 26 into two or more symmetrical or asymmetrical portions (e.g, halves).

In some embodiments, the sheath 26 has a separable lip forming the locking structure 70, allowing engagement of the sheath 26 with other elements described above, such as the needle 22, while allowing separation along split line 68. Additional embodiments of a splittable sheath body and/or hub that can be employed with the sheath 26 are shown and described, for example, in FIGS. 23A-23B, and the corresponding supporting text (e.g., paragraphs [0225]-[0229]), of U.S. patent application Ser. No. 13/319,998, entitled "ACCESS DEVICE WITH VALVE," filed Nov. 10, 2011, published as US 2012/0065590 on Mar. 15, 2012, the entire contents of which is incorporated by reference herein. In some applications, the wings 66 are sized to provide the healthcare provider with leverage for breaking apart the sheath hub 60. The sheath hub 60 and/or the sheath body 58 may comprise two or more portions (e.g., halves) connected by a thin (e.g., frangible) membrane. The membrane can be sized to hold the two or more portions of the sheath hub 60 and/or sheath body 58 together until the healthcare provider decides to remove the sheath hub 60 and/or sheath body 58 from the access device 20. The healthcare provider manipulates the wings 66 to break the membrane and sever one or more portions of the sheath hub 60 into separate or partially separated pieces.

Figure 5:
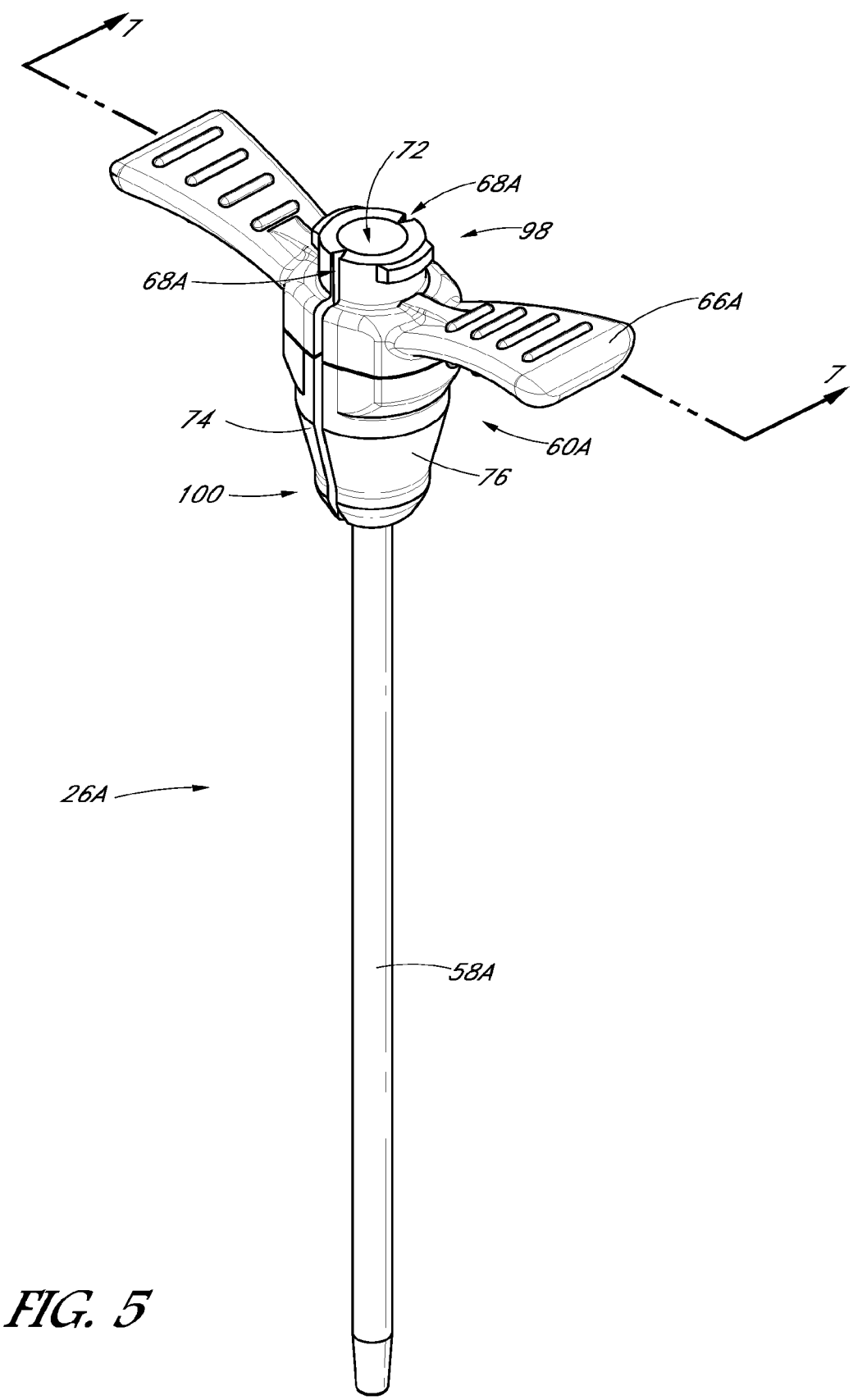
FIGS. 5 and 6 are a side isometric view and an exploded side isometric view, respectively, of another embodiment of the sheath from FIG. 1 that includes a valve element.
Figure 6:
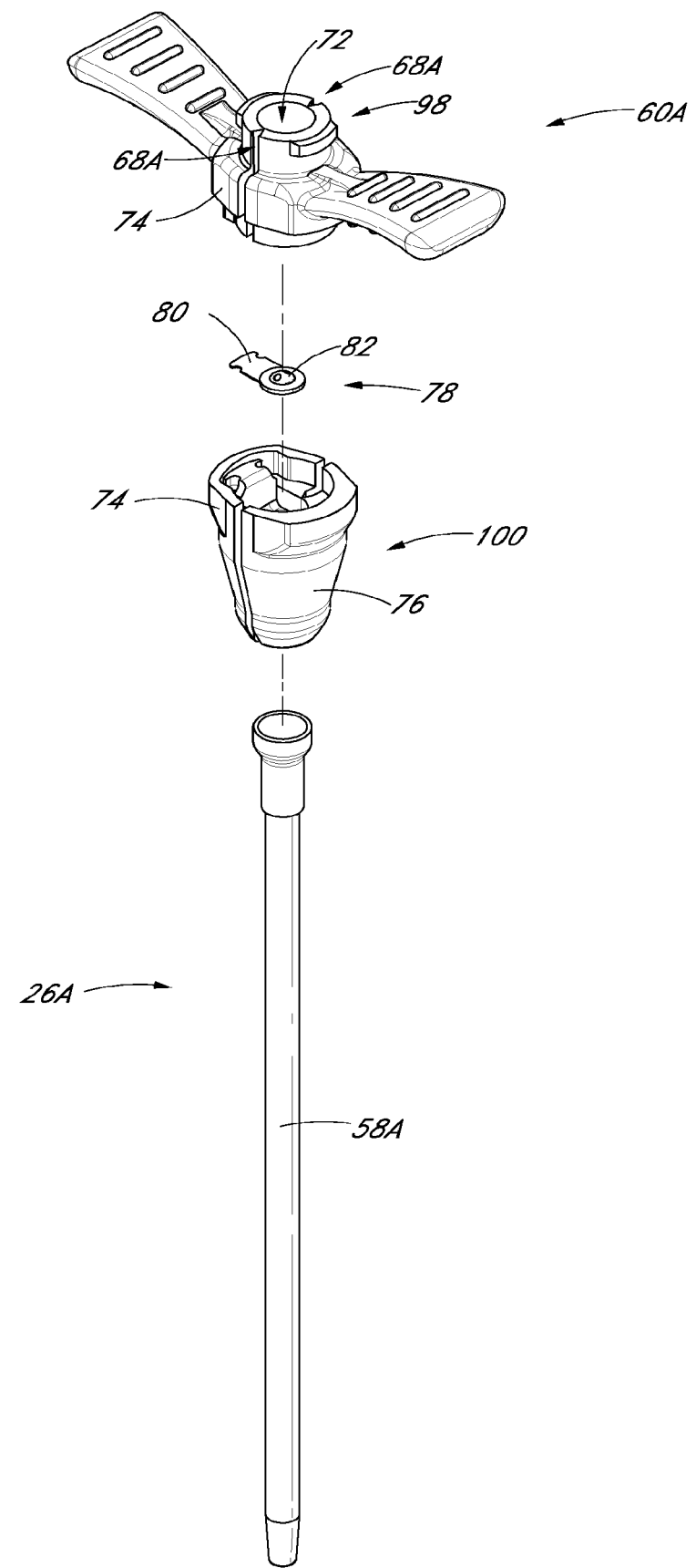

FIGS. 5-9 illustrate another embodiment of a sheath 26A that can be used with the needles, guide wires, and other elements described herein in a similar manner to the previously described sheath 26. The sheath 26A illustrated in FIGS. 5-9 includes a valve element 78. FIGS. 5 and 6 are a side isometric view and an exploded side isometric view, respectively, of the sheath 26A from FIG. 1. FIG. 7 is a side cross-sectional view of the sheath 26A of FIG. 5 taken at 7-7. FIGS. 8 and 9 are enlarged views of a section of the sheath 26A of FIG. 7 showing the valve element 78 in a closed and opened position, respectively.

Sheath 26A can include a sheath body 58A and a sheath hub 60A, with an inner cavity 72 extending through or along a portion of sheath body 58A and/or sheath hub 60A (e.g., along one or more longitudinal axes thereof). The sheath hub 60A can extend from a proximal end of the sheath body 58A. The sheath body 58A and/or sheath hub 60A can be optionally splittable along one or more split lines 68A. In some embodiments, the sheath body 58A and/or sheath hub 60A can be splittable along two or more split lines 68A, to form two or more separable sections or halves, such as sheath hub sections 74 and 76. The embodiments of the sheath 26A, including body 58A and hub 60A, can be generally similar to the embodiments of sheaths, sheath bodies, and/or sheath hubs discussed elsewhere herein.

With reference to FIGS. 6-9, the sheath 26A can include a valve element 78 configured to substantially seal a portion of inner cavity 72. The valve element 78 can include a resilient plate 80 supporting a sealing element 82. The resilient plate 80 can be supported by a portion of the sheath body 58A and/or hub 60A such that a portion (e.g., a sealing portion 84) of the resilient plate 80 can extend (e.g., radially inwardly) into and substantially seal the inner cavity 72. The valve element 78 can be positioned between a proximal portion 86 of the inner cavity 72 and a distal portion 88 of the inner cavity 72, such that the proximal portion 86 and the distal portion 88 can be substantially sealed with respect to each other. The portions 86, 88 can comprise any of a variety of sizes and shapes, and are shown with an approximately circular cross-sectional shape for illustrative purposes only. In the depicted embodiment, the proximal portion 86 of the inner cavity 72 comprises at least a region having a cross-sectional area that is less than the distal portion 88, to facilitate sealing of the valve 78 against the portion 86, while allowing the valve 78 to flex and move distally into the distal portion 88, as described further herein. In this arrangement, the valve 78 can be configured to substantially inhibit flow through the inner cavity 72 in a proximal direction, while not substantially inhibiting the passage of articles such as a dilator or needle through the cavity.

The valve element 78 can be adapted to flex or move between a closed, or substantially sealed position (for example, as shown in FIGS. 7 and 8), and an open, or substantially unsealed position (for example, as shown in FIG. 9), through flexation or flexing of the resilient plate 80. The valve element 78 can move between an open and closed position through passage of a fluid (or gas), a device, or through an operation by a user (for example, using an external lever or other device attached to the resilient plate 80) In the closed position, a sealing surface 90 on a proximal surface of the sealing element 82 can contact or otherwise engage with a corresponding sealing surface 92 on a distal surface of at least one of the splittable sheath body and hub 58A, 60A. The interaction of the sealing surfaces 90 and 92 can inhibit passage through the cavity 72 in the proximal direction. Notably, pressure against the valve element 78 in a proximal direction can press the sealing surfaces 90 and 92 further together. In some embodiments, this mechanism can be sufficiently resilient to withstand pressures associated with human blood vessels to prevent a loss of blood through the valve. In some embodiments, the sealing element 82 includes a raised portion, such as substantially dome-shaped portion 94. The dome-shaped portion 94 can prevent or reduce the likelihood of contact between the sealing surface 90 and a device 96, when the device 96 is extended through cavity 72. For example, if the sheath 26A is stored with a device extended through the cavity 72, for example, the needle 22 as described herein, if the device 96 sets or sticks to another portion of the sheath 26A, it will do so to the raised portion 94, and not to a portion of the sealing surface 90. As such, the raised portion 94 can prevent damage to the sealing surface 90 of the sealing element 82 by extended forceful contact with the device 96, and thus extend the sealing capability and life of the valve element 78.

In some embodiments, the resilient plate 80 is configured such that the sealing surface 90 of the sealing element 82 is biased or preloaded against the sealing surface 92 of the splittable sheath body and/or hub such that the valve 78 is preloaded in the closed position. This biasing can enhance the above-described inhibition of passage of matter in the proximal direction. Additionally, the biasing can help the valve element 78 inhibit passage of matter such as the flow of fluid or gas (e.g., blood or air) or passage of a device in a distal direction (e.g., longitudinally) within the cavity 72. For example, the bias towards the closed position can be strong enough to resist a force (or cracking pressure) in the distal direction to open the valve element 78. In some embodiments, the preload or bias of the valve element 78 can be sufficient to prevent gas from being drawn distally through the cavity 72, and into a patient due to, for example, negative pressure created by a human during a normal pulse. Notably, drawing gas into a blood vessel can cause serious health effects such as an embolism.

The resilient plate 80 can comprise any of a variety of materials with sufficient rigidity to support the sealing element 82 and substantially seal the inner cavity 72, and with sufficient flexibility to allow the valve element 78 to flex or move between the open and closed positions described herein. The resilient plate 80 can comprise a bio-compatible metal or plastic, or various composites or combinations thereof. Preferably, the resilient plate 80 can comprise a material with reduced susceptibility to cold-setting, such that a needle, dilator, catheter, or other medical article can be extended through the cavity 72, with the valve element 78 in an open position, as described above, and packaged together for a period of time within the sheath 26A, without compromising the valve features (e.g., its flexibility and ability to seal the cavity 72 when in a closed position). In some embodiments, the resilient plate 80 can comprise, Nickel, Titanium, and/or steel (e.g., stainless steel, spring steel, etc.), or various alloys or combinations thereof. In some embodiments, the resilient plate 80 comprises NiTi (Nitinol), or NiTi SE. In some embodiments, the resilient plate 80 can comprise a shape-memory alloy to facilitate its movement between an opened and closed position and to prevent cold-setting for extended periods of time such as 2 years.

The sealing element 82 can comprise any of a variety of materials that can substantially seal the inner cavity 72 when in contact with or biased against the sealing surface 92. In some embodiments, the sealing element 82 can comprise metal, plastic, rubber, or other suitable biocompatible materials such as polyisoprene, silicone, polyurethane, or other elastic polymers. In some embodiments, the Shore A hardness of the sealing element 82 can be within a range of approximately 5 to 90, or in some embodiments, 10 to 70, or in some embodiments, approximately 15 to 50, or in some embodiments, approximately 30. In some embodiments, the sealing element 82 can be coated or include other surface treatments, such as a siliconized surface to facilitate low-friction sliding of various elements along its surface (such as device 96). Even further, in some embodiments the resilient plate 80 and the sealing element 82 can be formed of the same material, such that the valve element 78 can optionally be a single unitary piece.

The resilient plate 80 and/or element 82 can be formed in a number of different ways, such as molding (e.g., injection), stamping and the like, and can be formed separately or integrally. The resilient plate 80 and sealing element 82 can be attached to each other in a variety of ways, such as with adhesive, bonding (e.g., ultrasonic, thermal, etc.), fasteners, overmolding, and the like. A primer or non-stick coating or surface treatment can be applied to the plate 80 and/or sealing element 82 to facilitate their attachment to each other during the manufacturing thereof. In some embodiments, a plurality of plates 80 and/or elements 82 can be formed in a single molding or stamping step, with severable tabs to allow the plates 80 and/or elements 82 to be used individually. With respect to the bending properties of the resilient plate 80, described above, in some embodiments the resilient plate 80 can be pretreated to have certain mechanical characteristics prior to its combination with the sealing element 82.

The valve element 78, as depicted by way of the resilient plate 80, can attach to the sheath 26A by a variety of means. In some embodiments it can be glued or bonded to the sheath 26A. In other embodiments, the resilient plate 80 can attach to the sheath 26A by molding or overmolding. In further embodiments, the resilient plate 80 can be molded integrally with the sheath 26A (or a portion thereof such as the sheath hub half). When formed integrally, it may be desirable to give the hub 60A or body 58A a substantially greater thickness than the resilient plate 80, such that the hub or body maintains a higher rigidity. In other embodiments the resilient plate 80 can attach to the sheath 26A by a mechanical compression, such as where the sheath hub 60A or body 58A includes a groove that receives the plate, and allows it to be press-fit into position The resilient plate 80 can be attached to various portions of the sheath hub 60A and/or body 58A. In some embodiments, the sheath hub 60A and/or body 58A can comprise two or more separate pieces that are positioned and attached with respect to each other such that a portion of the resilient plate 80 is clamped between a portion of the sheath hub 60A and/or body 58A. As best shown in FIGS. 6, 8, and 9, the sheath hub 60A can comprise a proximal portion 98 and a distal portion 100. The proximal portion 98 and the distal portion 100 are configured to engage with each other such that the valve element 78, by way of a mounting portion 102 of the resilient plate 80, can be supported or clamped therebetween within a groove or gap 104 (as shown in FIG. 9). Portions 98, 100 can comprise any of the materials described herein generally for the sheath 26A and other components thereof, such as the sheath hub 60A and the sheath body 58A. In one embodiment, the portion 98 comprises ABS plastic. In one embodiment, the portion 100 comprises a K resin. The portions 98, 100 can engage with each other using any of a variety of attachment means and methods known or described herein, such as bonding, adhesive (e.g., solvents), and the like.

The valve element 78, and resilient plate 80, can be attached to one or more sections of the sheath hub 60A and/or body 58A that separate along line(s) 68A. Preferably, the resilient plate 80 is attached to only one separable section of the sheath 26A, such as sheath hub section 74, to facilitate the separation of the valve 78 from the sheath hub section 76 during the splitting of sheath 26A. Additionally, the plate 80 can be attached to only one separable section of the sheath 26A to facilitate the flexing and movement of the resilient plate 80 and the sealing element 82 within the inner cavity 72. In other embodiments, where the valve element 78 is attached to multiple separable portions of the sheath hub 60A and/or body 58A, the valve element 78 can also be separable by similar structures.

FIGS. 10, 11, and 12 are enlarged views of a section of an embodiment of the sheath 26A that includes an annular member 106, a resilient plate 80A, and sealing element 82A. The plate 80A and sealing element 82A can be similar to the resilient plate 80 and sealing element 82 shown in FIGS. 6-9 and described herein. The annular member 106 can function like an O-ring in some respects. As shown, the annular member 106 includes a central bore 108 configured to receive the domed-shaped portion 94A of the sealing element 82A when the valve is in a closed position. A top surface of the annular member 106 tapers so that the annular member is thinner proximate the bore 108 than at a location outward of the bore 108, e.g., at the outer edge. The taper can be downwardly from an upper surface in some embodiments. A bottom surface of the annular member 106 can be substantially straight or flat. The annular member 106 is placed against the sealing surface 92 so that in a closed position, the sealing element 82A seals against the annular member 106 rather than the sealing surface 92. The annular member 106 can be made of a relatively soft material, and can be thin enough to tear during splitting of the sheath 26A. The annular member 106 can advantageously compensate for possible molding imperfections and/or misalignment in the manufacture and assembly of the sheath hub, for example, due to being constructed from a relatively soft and compliant material. The annular member 106 also advantageously reduces the size of the aperture to be sealed by the sealing element 82A compared to the sealing surface 92, which can produce a greater vacuum hold to bias the sealing element 82A in a closed position with the same spring pre-loading force of the resilient plate 80A. Additionally, the annular member 106 can act as a seal around a device introduced into the patient through the sheath 26A to maintain a seal when the valve 78 is in an open position to accommodate the device. The annular member 106 can therefore act as a seal independent of the sealing element 82A. In some embodiments, the annular member 106 can stretch to accommodate and/or conform to various devices that can be introduced through the sheath 26A.

In some embodiments, the sealing element 82A can be made of a relatively hard material, for example, polyurethane or polycarbonate. Inclusion of a relatively soft annular member 106 can advantageously allow the sealing element 82A to be made of a relatively hard material because the more compliant annular member 106 can compensate for molding imperfections, misalignment, and the like for which a relatively hard sealing element 82A may not be able to compensate as effectively. The relatively hard material can advantageously reduce possible damage to the resilient plate 80A. Additionally, with a sealing element 82A made of a relatively softer material, for example, silicone, the resilient plate 80A may bend to some extent anywhere along its length when the valve is opened with a sealing element 82A made of a relatively harder material, bending of the resilient plate 80A may be relatively more limited to a pivot axis 110, which can reduce possible damage and/or wear to the resilient plate 80A. The relatively hard material can also better resist tearing and/or other wear. Such tearing or wear can adversely affect the effectiveness of the seal or expose sharp portions of the resilient plate 80A, which can cut or otherwise damage other instruments, for example a dilator as described herein, inserted into and/or removed from the sheath 26A through the valve 78.

FIG. 13 is a cross-section view of the syringe 24 from FIG. 1 in combination with the sheath 26A from FIG. 5 and shows a plunger 32 of the syringe 24 in an advanced state. The sheath 26A illustrated in FIG. 13 includes a valve element 78. FIG. 14 is similar to FIG. 13 except the plunger 32 of the syringe 24 is in a retracted state. FIG. 15 is an enlarged cross-section view from FIG. 13 taken at 15-15. With reference to FIGS. 13-15, the second needle hub 52 is disposed on a distal end of the interior needle portion 46. The second needle hub 52 can include a locking structure 112 at a proximal part of the second needle hub 52 to allow the physician or healthcare provider to lock the second needle hub 52 to the barrel tip 38. Of course the access device 20 could be provided to the physician with the second needle hub 52 already locked to the barrel tip 38.

Similarly, the first needle hub 50 is disposed on a proximal end of the exterior needle portion 42. The first needle hub 50 can include a locking structure 114 at a proximal part of the first needle hub 50 to allow the physician or healthcare provider to lock the first needle hub 50 to the second needle hub 52. The first needle hub 50 can also include a locking structure 64 at a distal portion of the first needle hub 50 to allow the physician or healthcare provide to secure (e.g., releasably secure) another medical article such as sheath hub 60 to the first needle hub 50. The locking structures 112, 114 can be, for example, Luer lock or Luer slip connection.

Although in some embodiments the first needle hub 50, the second needle hub 52, and/or the sheath hub 60 can connect via one or more luer connections that may prevent the passage of gases, additional mechanisms known in the art or described herein can also attach one or more of the structures. For example, in the depicted embodiment the first needle hub 50 can include locking structure 64 that can releasably hook to the locking structure 70 on a ledge portion or lip of the sheath hub 60. In some embodiments, a taper within the sheath 26, 26A (also used for a luer connection with a needle) can facilitate a seal between the sheath 26, 26A and the first needle hub 50.

The syringe barrel 30 includes the fluid chamber 34 with the plunger 32 movable between advanced and retracted states slideably disposed within the fluid chamber 34. The central channel 56 includes the aperture 48 disposed in the fluid chamber 34. The central channel 56 is formed longitudinally through the hollow syringe barrel 30 and plunger 32. The valve 116 is disposed in operative relationship relative to the central channel 56 to prevent passage of fluid through the central channel 56 during flushing or aspirating of the access device 20 or during the introduction or withdrawal of a guide wire 28 through the central channel 56. Fluid is permitted to flow from the patient's body into the fluid chamber 34 through the aperture 48. The central channel 56 is configured to maintain the guide wire 28 in a substantially straight configuration while the guide wire 28 is disposed within the central channel 56.

The exterior needle portion 42 has a sufficiently long length to access a targeted subcutaneous body space and has a sufficient gauge size to withstand the insertion forces when accessing the body space without causing undue trauma. For many applications, the needle body can have a length between 3-20 cm, and more preferably between 3-10 cm. For example, to access a body space (e.g., a vessel) in the thorax of an adult human, the exterior needle portion 42 preferably has a length of 7 cm or greater, and more preferably has a length of 9 cm or greater, and most preferably has a length of 9 to 10 cm. The size of the needle preferably is 18 gauge or smaller, and more preferably between 18-28 gauge, and most preferably between 18-26 gauge for micro-puncture applications (e.g., peripheral IVs). For applications with a neonate, the length and gauge of the exterior needle portion 42 should be significantly shorter and smaller, for example preferably between 3-4 cm and between 26-28 gauge. In some embodiments, the exterior needle body 42 includes an echogenic portion that can be used in combination with ultrasound to help position the needle in the desired location.

The plunger 32 comprises a valve 116 and a central channel 56 formed therethrough. The inner end of the plunger 32 is received within the barrel 30, while the opposite end includes the finger grasping element 40. The valve 116 can comprise one or more one-way valve elements. For example, the valve elements may comprise a flexible resilient hollow hemispheric member. A normally closed centrally disposed slit or aperture is formed in the center of the valve element.

In use the access device 20 is aspirated by the retraction of the plunger 32 as shown in FIG. 14 permitting fluid to pass into the interior of the barrel 30 through the aperture 48. During aspiration air is prevented from entering the central channel 56 by the valve 116. Once aspirated, the access device 20 may then be flushed. While flushing, the valve 116 prevents liquid from passing through the central channel 56 into the valve 116. Thus, the access device 20 functions as an ordinary syringe.

As shown in FIG. 14 when the plunger 32 is retracted, the interior needle portion 46 of the needle 22 remains disposed within the central channel 56. In this configuration the guide wire 28 may be passed through the access device 20 and into the blood vessel or body cavity. The guide wire 28 passes through the centrally disposed slot formed in the valve 116 which forms a seal therewith to prevent either liquid or air from passing through the valve 116 during the introduction of the guide wire 28.

Figure 16:
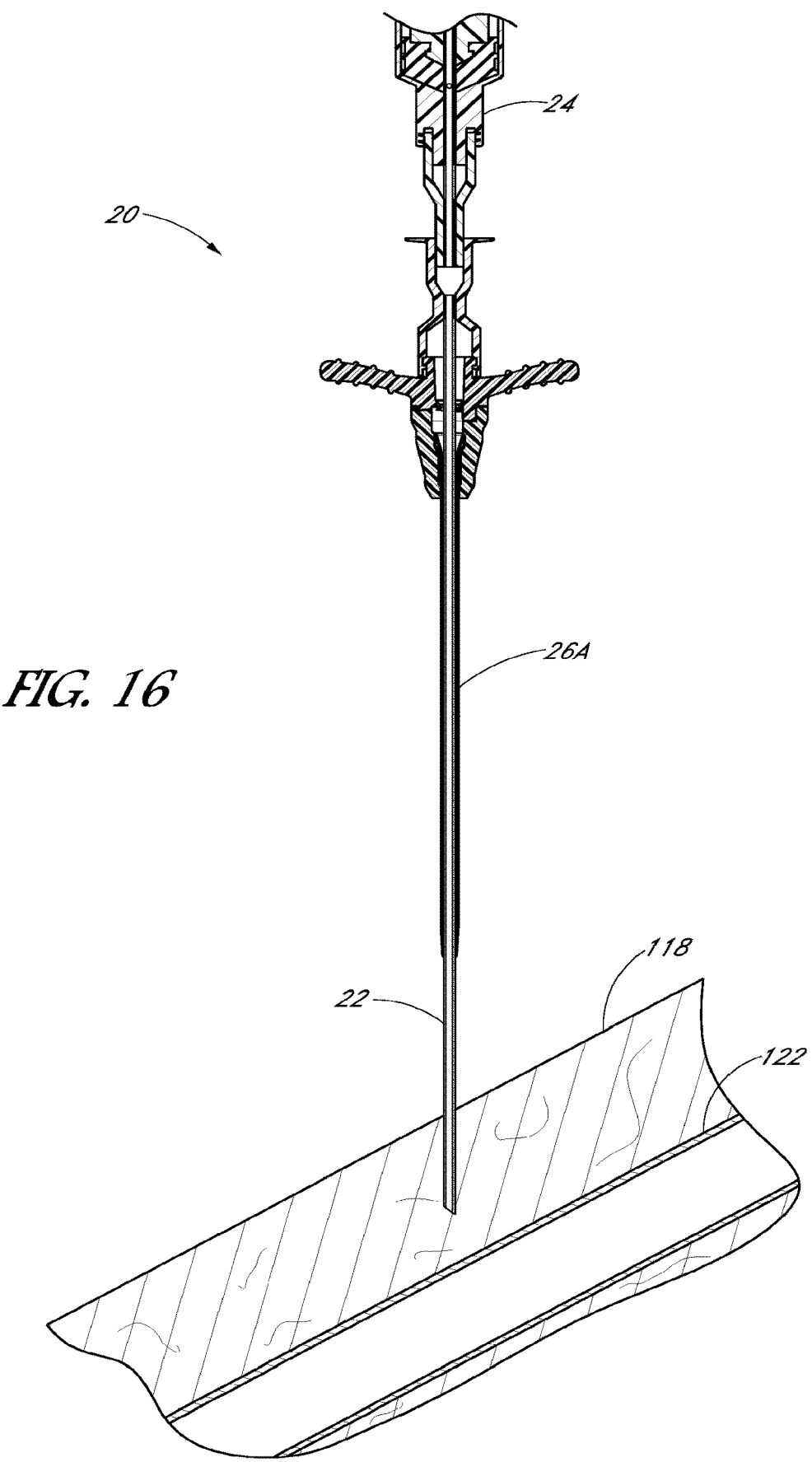
FIG. 16 is a cross-section view of the access device illustrated in FIG. 13 penetrating a body.
Figures 17A, 17B:
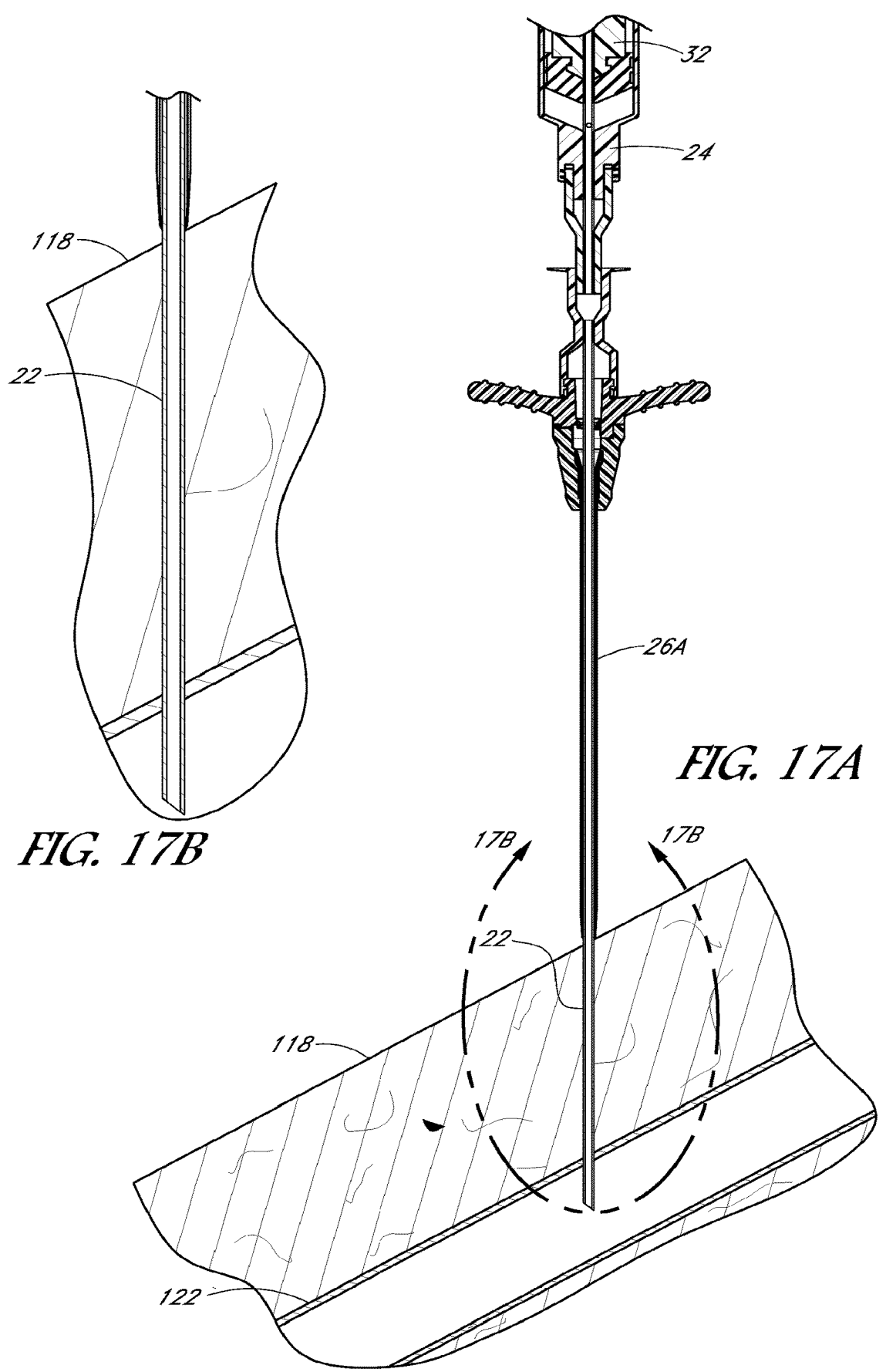
FIG. 17A is a cross-section view similar to FIG. 16 except the needle has penetrated the vasculature and the plunger has been partially retracted creating a negative pressure in the syringe body.
FIG. 17B is an enlarged partial cross-section view from FIG. 17A of a distal end of the needle.

FIG. 16 is a cross-section view of the access device 20 illustrated in FIG. 13 penetrating a body 118. FIG. 17A is a cross-section view similar to FIG. 16 except the needle 22 has penetrated the vasculature and the plunger 32 has been partially retracted creating a negative pressure in the syringe barrel 30. At this stage of use, a channel is formed between the needle 22 and the syringe 24, to allow, for example, blood to flow into the fluid chamber 34. The aperture 48 in the interior needle portion 46 allows blood to flow through the sidewall of the needle 22 and into the fluid chamber 34. FIG. 17B is an enlarged partial cross-section view from FIG. 17A of a distal end of the needle 22. In use, the piercing point 44 enters the blood vessel 122. When entering an artery, the arterial blood pressure causes the plunger 32 to retract as the blood enters the fluid chamber 34 through the aperture 48. When cannulating the blood vessel 122, the access device 20 is aspirated by the retraction of the plunger 32 to create a vacuum or negative pressure within the fluid chamber 34 permitting fluid to pass into the barrel 30 through the aperture 48. In certain embodiments, the physician or healthcare provider can insert a transduction probe in the rear of the syringe 24 and through the valve 116 as known in the art. The physician or healthcare provider can observe a wave form associated with the probe to determine if venous access has been achieved.

FIG. 18A is a cross-section view similar to FIG. 17 except a guide wire 28 has been fed through the plunger 32, the valve 116, and needle 22 and into the blood vessel 122 of the patient. Once the physician or healthcare provider has located the needle 22 within the target blood vessel 122, the physical or healthcare provider feeds the guide wire 28 through the plunger 32 while maintain the position of the plunger 32 relative to the barrel 30. Preferably the needle 22 is also held still while the guide wire 28 is fed through the syringe 24 and into the patient. During the insertion procedure, the valve 116 seals against the guide wire 28 preventing air from entering the central channel 56 to maintain the negative pressure in the fluid chamber 34. A guide wire advancer as known in the art may be employed when feeding the guide wire 28 through the syringe 24. For example, if the guide wire 28 has a curved or J tip, an advancer may be employed to straighten the tip facilitating feeding of the guide wire 28 into the central channel 56 of the plunger 32. FIG. 18B is a cross-section view similar to FIG. 18A except the guide wire 28 has been extended further into the vasculature of the patient.

Figure 19:
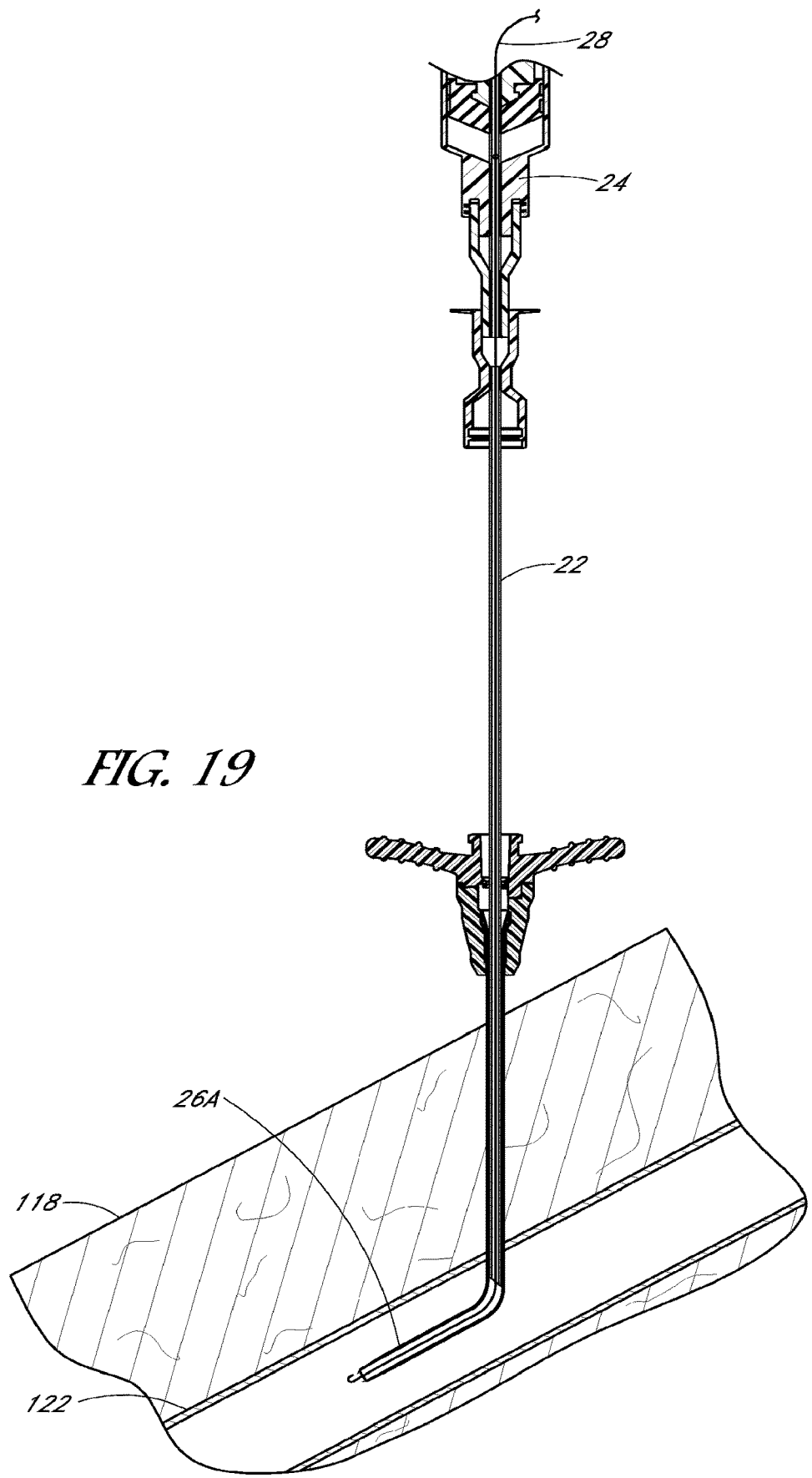
FIG. 19 is a cross-section view similar to FIG. 18B except the sheath has been slid along the exterior portion of the needle and into the patient's vasculature.

FIG. 19 is a cross-section view similar to FIG. 18B except the sheath 26A has been slid along the exterior portion 42 of the needle 22 and into the patient's vasculature. During insertion of the sheath 26A over the needle 22, guide wire 28 and into the blood vessel 122, the existing negative pressure in the syringe 24 ensures that any air located between the inside diameter of the sheath 26A and the outside diameter of the needle 22 is drawn into the needle 22 rather than into the blood vessel 122. If necessary, a skin-nick can be performed to enlarge the puncture site adjacent to the needle 22.

Figure 20:
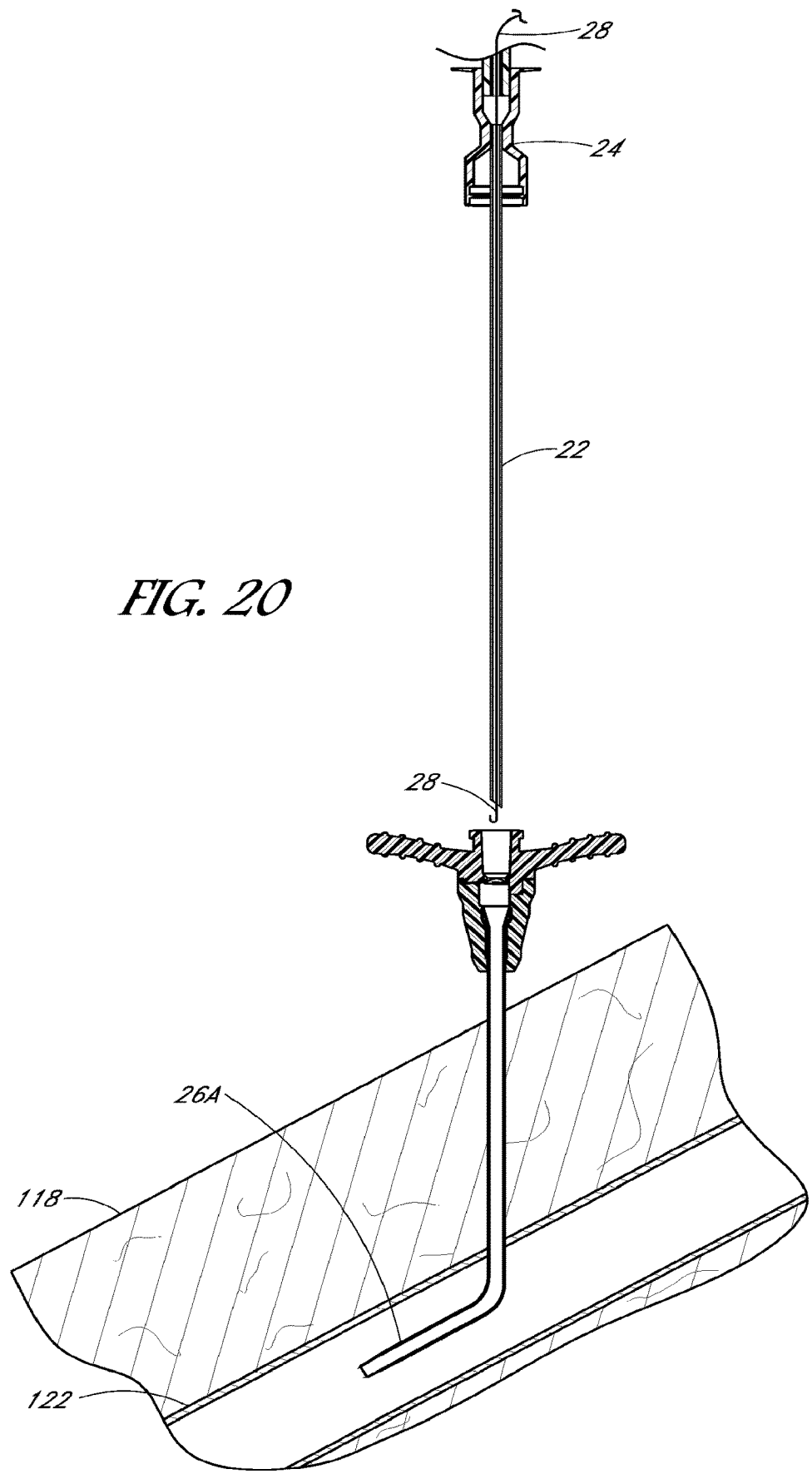
FIG. 20 is a cross-section view similar to FIG. 19 except the syringe and guide wire have been removed from the patient and the sheath.

FIG. 20 is a cross-section view similar to FIG. 19 except the syringe 24 and guide wire 28 have been removed from the patient leaving the sheath 26A properly inserted within the blood vessel 122. During the removal process, the internal volume of the stationary sheath 26A increases as the needle 22 and guide wire 28 are removed which creates negative pressure in the sheath 26A ensuring air is not drawn into the blood vessel 122 during removal.

The described procedure is less time intensive than the Raulerson syringe techniques and does not require multiple exchanges over the guide wire when employed with multiple medical articles (e.g., dilator over guide wire, sheath over guide wire, catheter over guide wire). If such exchanges were performed over the guide wire, such actions present the risk of losing cannulation, lost guide wire, and contamination. Further, during the skin-nick step the needle 22 protects the guide wire 28 from being accidently severed. The described technique reduces the risk of movement of the sheath 26, 26A and guide wire 28 relative to the patient during the procedure. The above described procedure is less bloody, especially if a valved sheath 26A is employed, and reduces the exposure of the physician or healthcare provider to blood.

Figure 22:
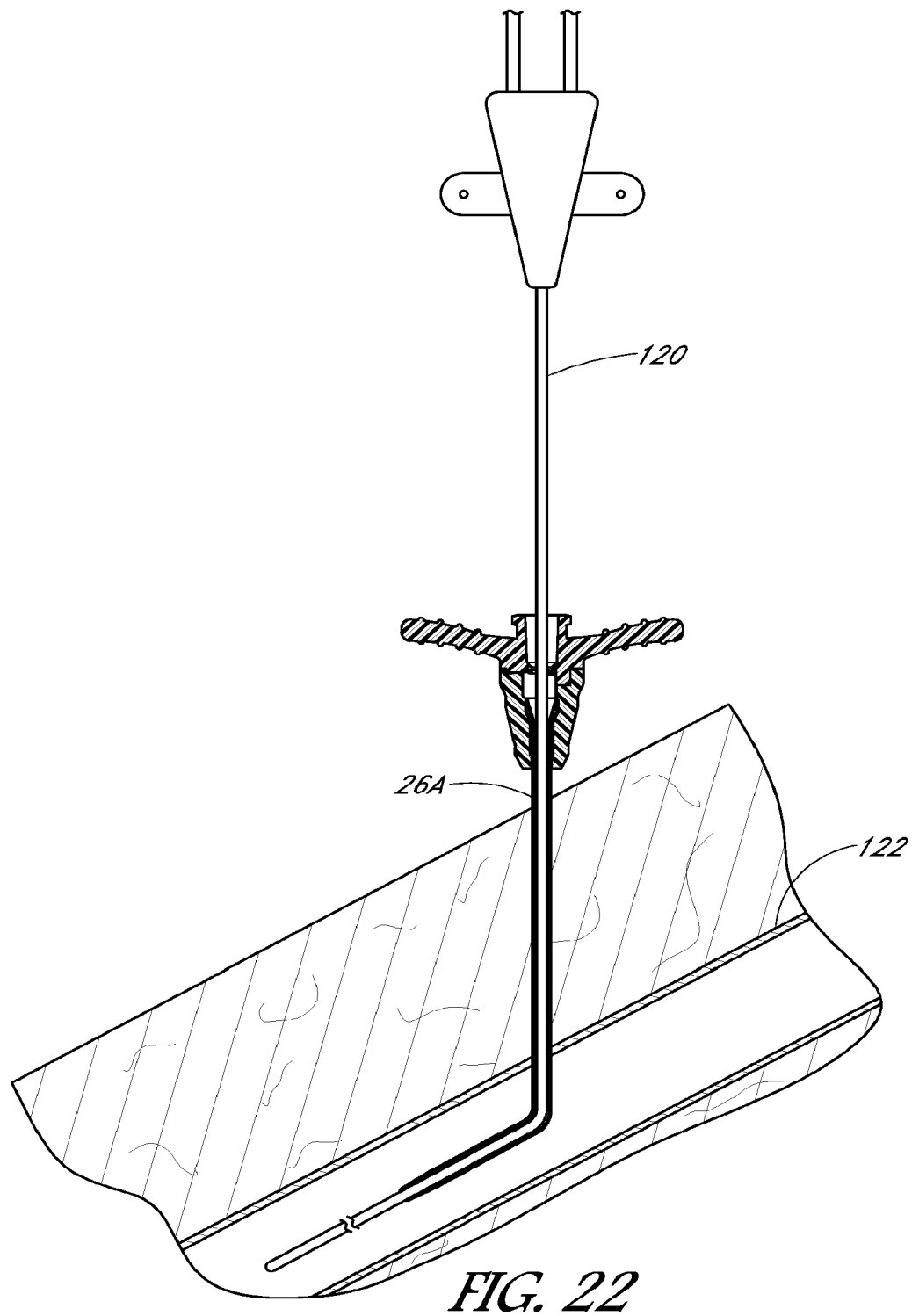
FIG. 22 is a cross-section view similar to FIG. 21 except the catheter has been inserted through the sheath and into the patient's vasculature.

FIG. 21 is a cross-section view similar to FIG. 20 except a catheter 120 is aligned with the sheath 26A for insertion into the patient's vasculature. FIG. 22 is a cross-section view similar to FIG. 21 except the catheter 120 has been inserted through the sheath 2GA and into the patient's vasculature, specifically the targeted blood vessel 122.

Figure 23:
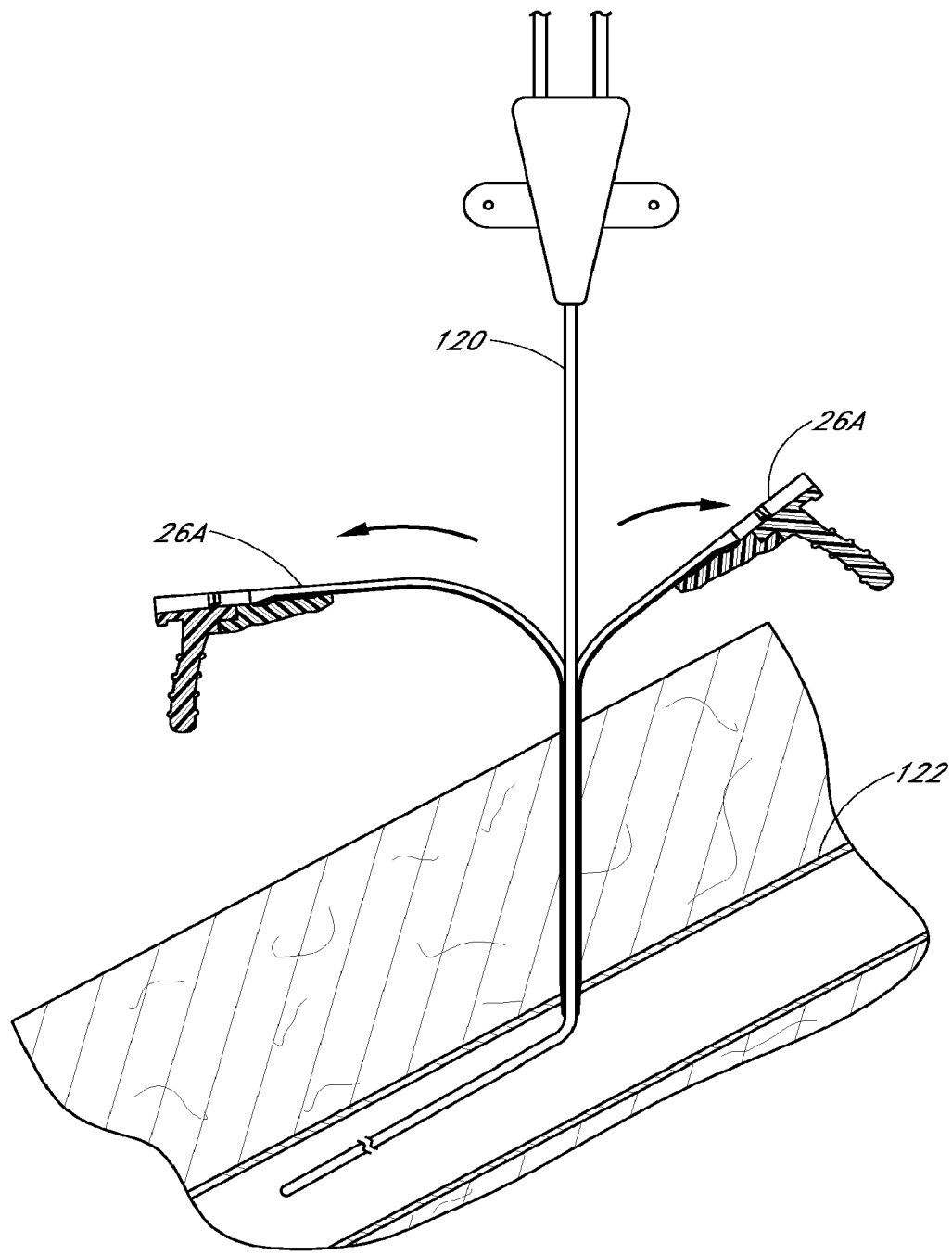
FIG. 23 is a cross-section view similar to FIG. 22 except two portions of the sheath are being peeled away from each other to remove the sheath from encircling the catheter.

FIG. 23 is a cross-section view similar to FIG. 22 except two portions of the sheath 26A are being peeled away from each other to remove the sheath 26A from encircling the catheter 120. The sheath 26A is splittable along one or more split lines 68, 68A (see FIGS. 4 and 5). A splittable sheath 26A provides the advantage of allowing a portion of or the entire sheath body 58 to be removed depending on the type of catheter or medical article that is to be inserted into the vessel after employing the access device 20. For example, after the catheter 120 is inserted into the blood vessel 122, a portion of the sheath body 58 is separated or peeled-away and removed to reduce clutter at the access site. The peel-away sheath 26A can be first slid in a proximal direction along the catheter 120 until the sheath 26A is removed from the patient and then split apart. Alternatively, the sheath 26A can be initially split prior to the entire sheath 26A being removed from the patient. After the remainder of the sheath 26A is removed from the patient, the physician or healthcare provided can continue splitting the sheath 26A. Of course, the sheath 26A could be split in concert with its removal from the patient as is illustrated in FIG. 23. In certain embodiments, the sheath 26A is not splittable.

FIG. 24 is a plan view of a dilator 124 that can be used with the access device 20 of FIG. 1 to facilitate insertion of a larger sheath 26, 26A into the vasculature. In such an embodiment, the dilator 124 is disposed between the needle 22 and the sheath 26, 26A. FIG. 25 is a cross-sectional view taken along the lines 25-25 in FIG. 24.

Figure 26:
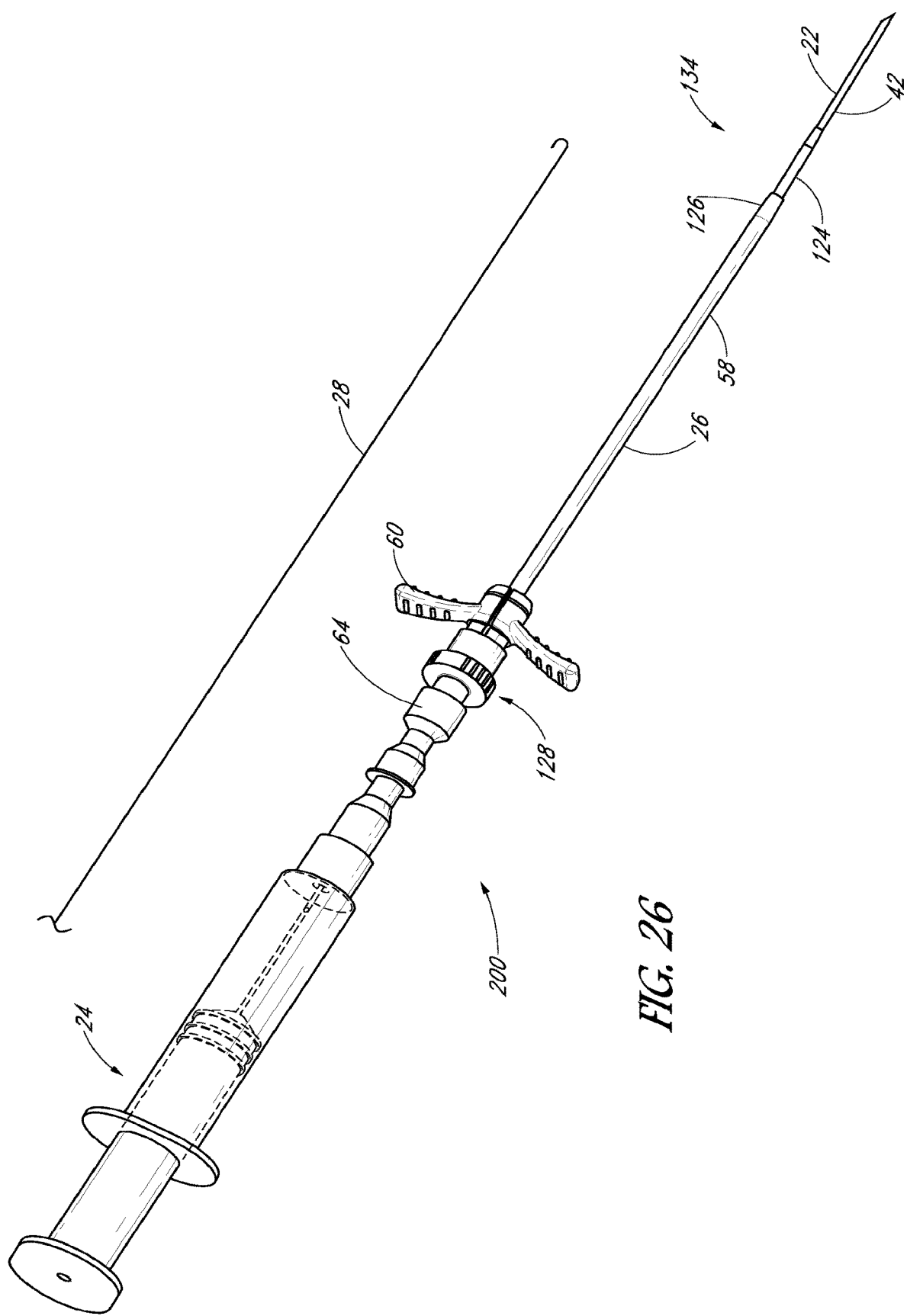
FIG. 26 is a perspective view of an embodiment of an access device having a syringe with a needle coaxially aligned with medical articles such as a sheath and a dilator. A guide wire for use with the access device is also shown.
Figure 27:
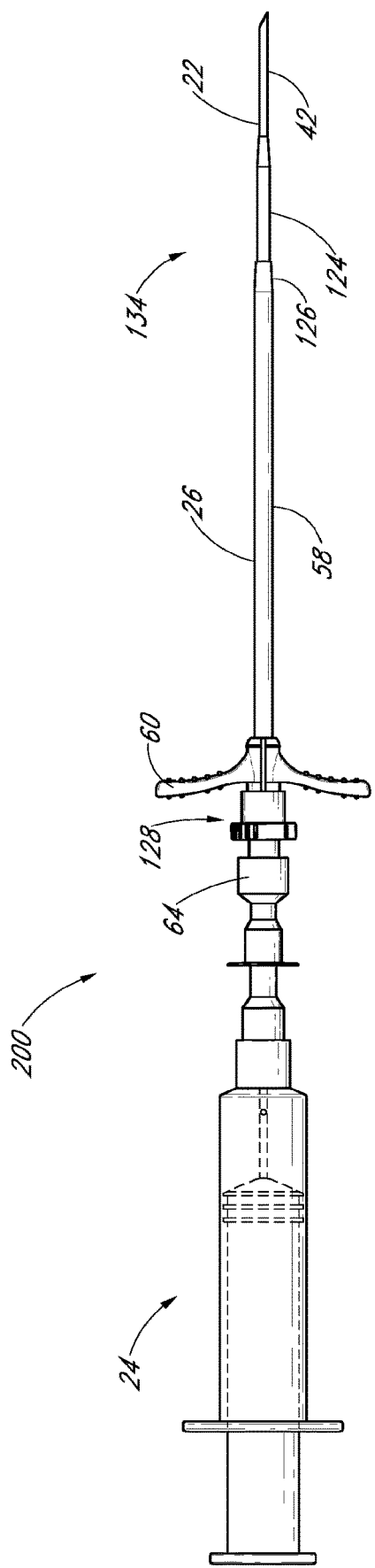
FIG. 27 is a plan view of the embodiment depicted in FIG. 26 without the guide wire.

FIG. 26 is a perspective view of an embodiment of an access device 200 similar to the access device 20 except the access device 200 includes the dilator 124 illustrated in FIGS. 24 and 25. The dilator 124 is disposed between the needle 22 and the sheath 26, 26A. Thus, the access device 200 has a syringe 24 with a needle 22 coaxially aligned with the sheath 26 and the dilator 124. The guide wire 28 for use with the access device 200 is also shown. FIG. 27 is a plan view of the embodiment depicted in FIG. 26. With reference to FIGS. 26 and 27, an example embodiment of the access device 200 includes the needle 22, the syringe 24, the dilator 124, and the tubular sheath 26. In the illustrated embodiment, the access device 200 also includes the guide wire 28. The dilator 124 can be coaxially disposed about the needle 22. The sheath 26 can be coaxially disposed about the dilator 124. The dilator 124 expands an opening or passage created by the needle 22. The expanded passage facilitates subsequent introduction of the sheath 26. The access device 200 allows the introduction of the guide wire 28, and subsequently the dilator 124 and finally the sheath 26 into a patient's body. The syringe 24 and sheath 26 are the same as the syringe 24 and sheath 26 described with respect to FIG. 1. In certain embodiments, the syringe 24 and sheath 29 include coupling structures to releasably couple to the dilator 124.

With reference to FIGS. 24 through 27, the dilator 124 is illustrated. The dilator 124 includes a generally flexible tubular structure, a proximal end or hub 128, and a distal end or body 134, and defines a lumen along a longitudinal axis. The dilator hub 128 is coupled with the proximal end of the dilator body 134 and has a passage therethrough.

The dilator hub 128 can include a first locking structure 130 to engage the locking structure 64 of the exterior needle portion 42 and a second locking structure 132 to engage with the sheath hub 60. In certain embodiments, the dilator hub 128 does not include locking structures. For example, a distal surface of the dilator hub 128 may abut against a proximal surface of the sheath hub 60 while a proximal surface of the dilator hub 128 abuts against a distal surface of the needle portion 42 of the syringe 24.

A distal portion 134 of the dilator body 126 can include a tapering outer surface which extends beyond a distal end of the sheath body 58. In this way, the distal portion 134 enters the skin and vasculature prior to the sheath body 58 entering the skin and vasculature. The tapering outer surface of the distal portion 134 gradually expands the puncture site to a larger size than created by the needle 22 to accommodate the distal end of the sheath body 58. Of course the dilator 124 is not required for use of the access device.

Figure 28:
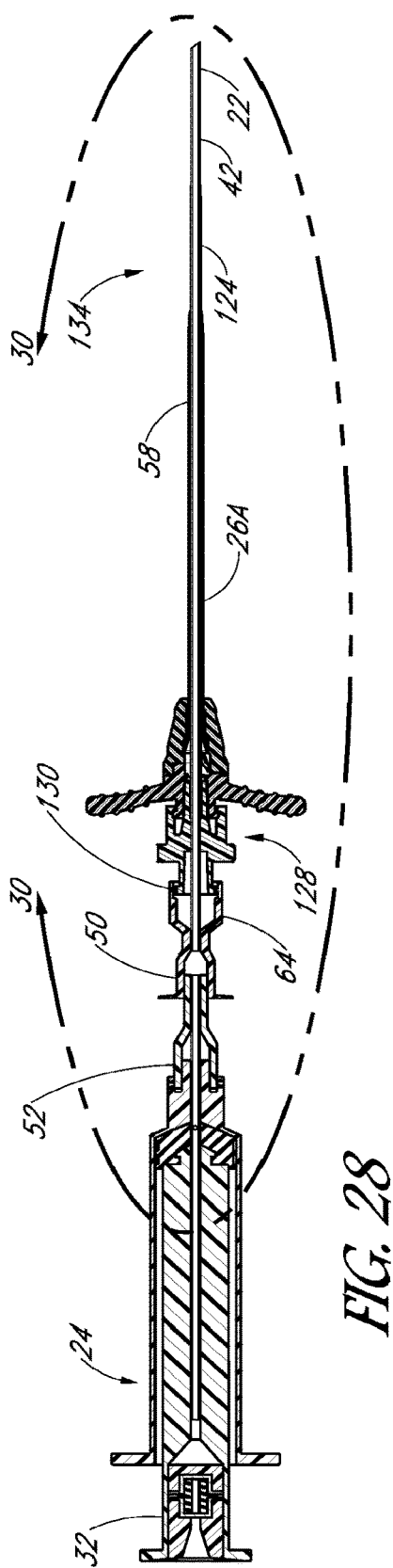
FIG. 28 is a cross-section view of the syringe from FIG. 26 and shows a plunger of the syringe in an advanced state.
Figure 29:
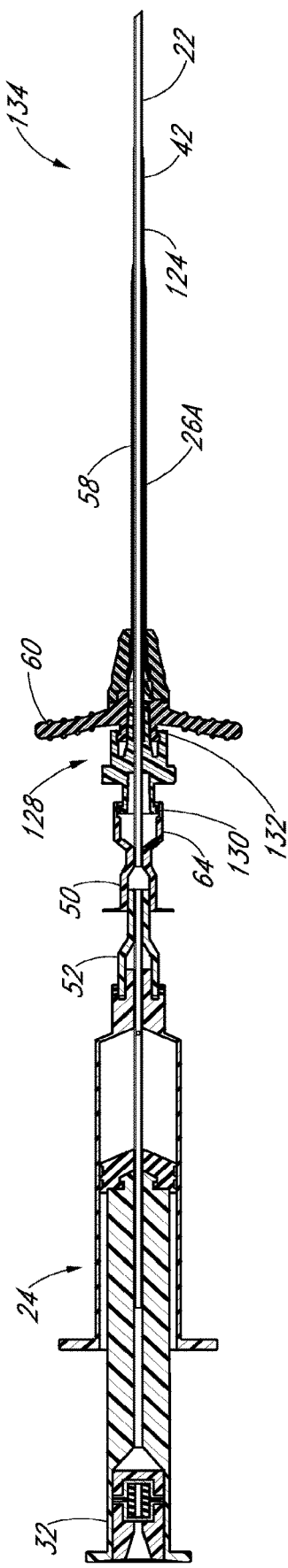
FIG. 29 is similar to FIG. 28 except the plunger of the syringe is in a retracted state.
Figure 30:
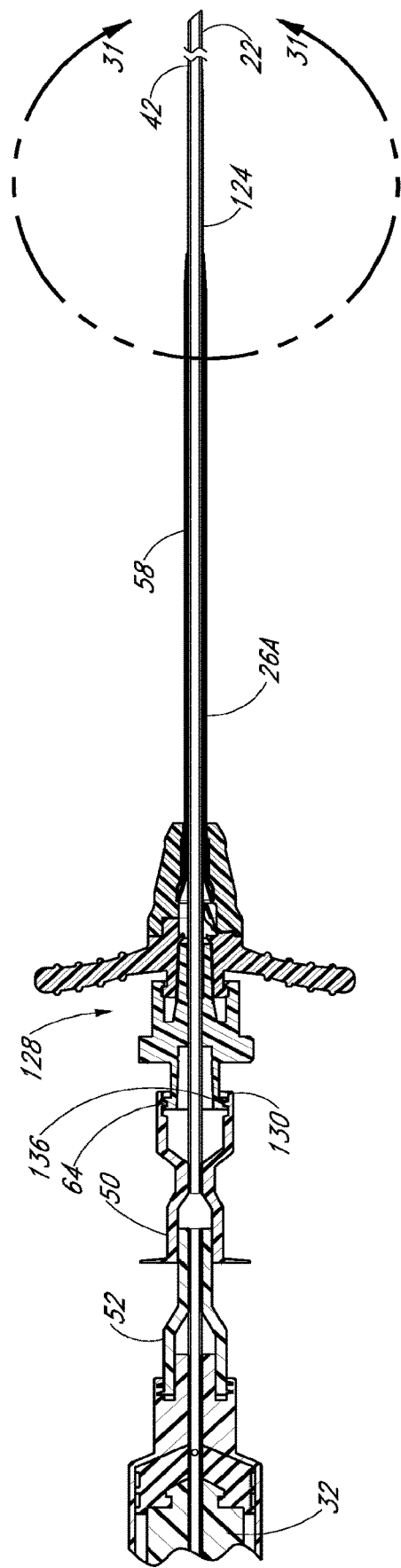
FIG. 30 is an enlarged cross-section view from FIG. 28 taken at 30-30.

FIG. 28 is a cross-section view of the syringe 24 from FIG. 26 and shows a plunger 32 of the syringe 24 in an advanced state. FIG. 29 is similar to FIG. 28 except the plunger 32 of the syringe 24 is in a retracted state. FIG. 31 is an enlarged cross-section view from FIG. 28 taken at 31-31. With reference to FIGS. 28-30, the first locking structure 130 of the dilator hub 128 is engaged with the locking structure 64 of the exterior needle portion 42 to allow the physician or healthcare provider to (e.g., releasably secure) lock the dilator 124 relative to the barrel tip 38. The second locking structure 132 of the dilator hub 128 is engaged with the sheath hub 60 to allow the physician or healthcare provider to secure (e.g., releasably secure) the dilator 124 relative to the sheath 26, 26A. Of course the access device 200 could be provided to the physician with the dilator 124 already locked to the exterior needle portion 42 and the sheath hub 60. The locking structures 130, 132 can be, for example, Luer lock or Luer slip connection.

Although in some embodiments the first needle hub 50, the second needle hub 52, the dilator hub 128 and/or the sheath hub 60 can connect via one or more luer connections that may prevent the passage of gases, additional mechanisms known in the art or described herein can also attach one or more of the structures. For example, in the depicted embodiment the first needle hub 50 can include locking structure 136 that can releasably hook to a ledge portion or lip of the dilator hub 128. In some embodiments, a taper within the dilator 124 can facilitate a seal between the dilator 124 and the first needle hub 50.

FIG. 32 is an enlarged cross-sectional view of the embodiment depicted in FIG. 31 taken at a longitudinal location wherein the needle 32, dilator 124, and sheath 26 overlap along line 32-32. FIG. 33A is a cross-section view of the access device 200 illustrated in FIG. 28 penetrating a body 118. The dilator 124 and the sheath 26A have yet to penetrate the body. FIG. 33B is an enlarged partial cross-section view from FIG. 33A of a distal end of the needle 22.

Figures 34A, 34B:
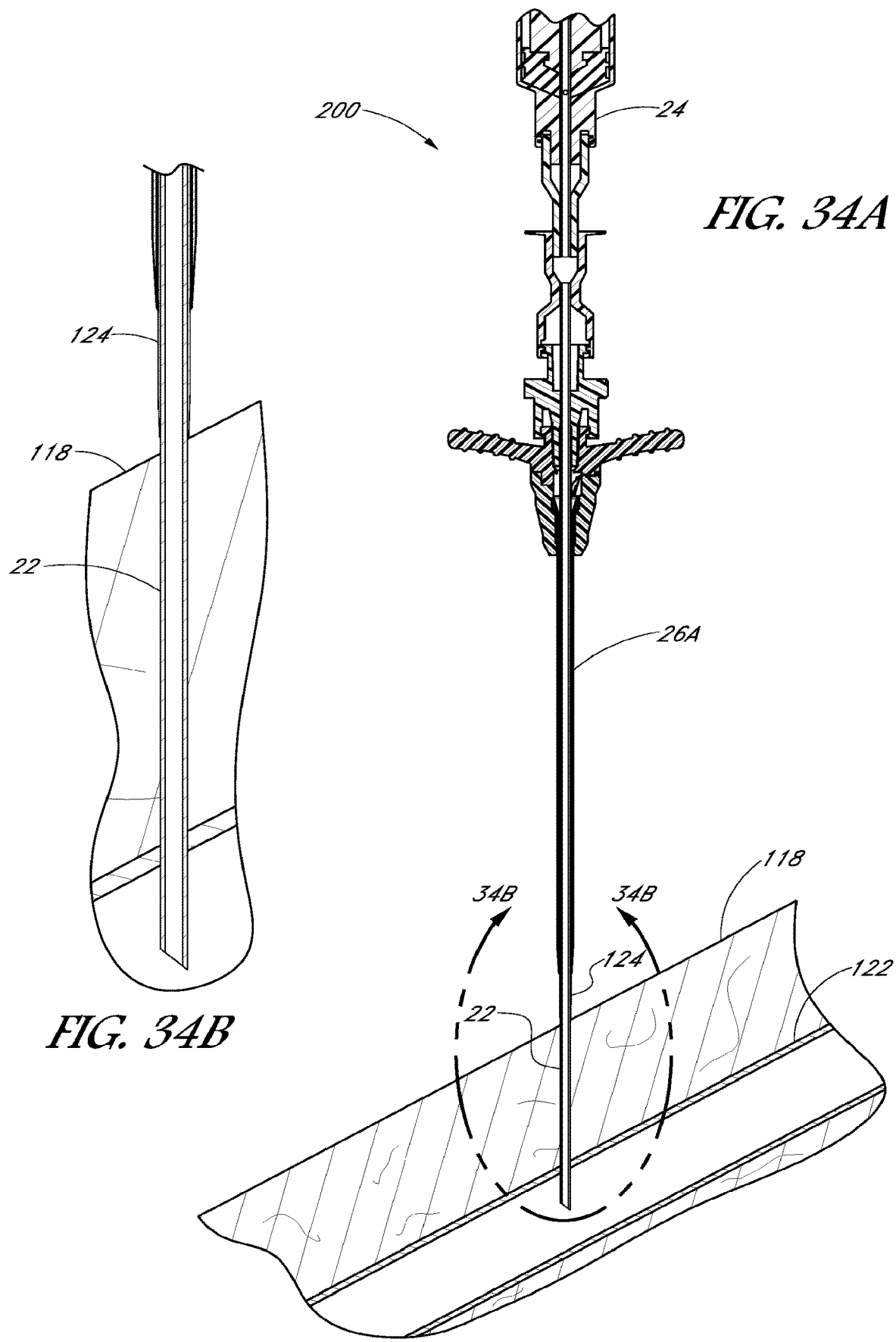
FIG. 34A is a cross-section view similar to FIG. 33A except the needle has penetrated the vasculature and the plunger has been partially retracted creating a negative pressure in the syringe body.
FIG. 34B is an enlarged partial cross-section view from FIG. 34A of a distal end of the needle.

In FIG. 34A, the needle 22 has penetrated the vasculature and the plunger 32 has been partially retracted creating a negative pressure in the syringe barrel 30. The dilator 124 and the sheath 26A have yet to penetrate the vasculature. At this stage of use, a channel is formed between the needle 22 and the syringe 24, to allow, for example, blood to flow into the fluid chamber 34. The aperture 48 in the interior needle portion 46 allows blood to flow through the sidewall of the needle 22 and into the fluid chamber 34. FIG. 34B is an enlarged partial cross-section view from FIG. 34A of a distal end of the needle 22. In use, the piercing point 44 enters the blood vessel 122. When entering an artery, the arterial blood pressure causes the plunger 32 to retract as the blood enters the fluid chamber 34 through the aperture 48. When cannulating the blood vessel 122, the access device 20 is aspirated by the retraction of the plunger 32 to create a vacuum or negative pressure within the fluid chamber 34 permitting fluid to pass into the barrel 30 through the aperture 48. In certain embodiments, the physician or healthcare provider can insert a transduction probe in the rear of the syringe 24 and through the valve 116 as known in the art. The physician or healthcare provider can observe a wave form associated with the probe to determine if venous access has been achieved.

Figure 35B:
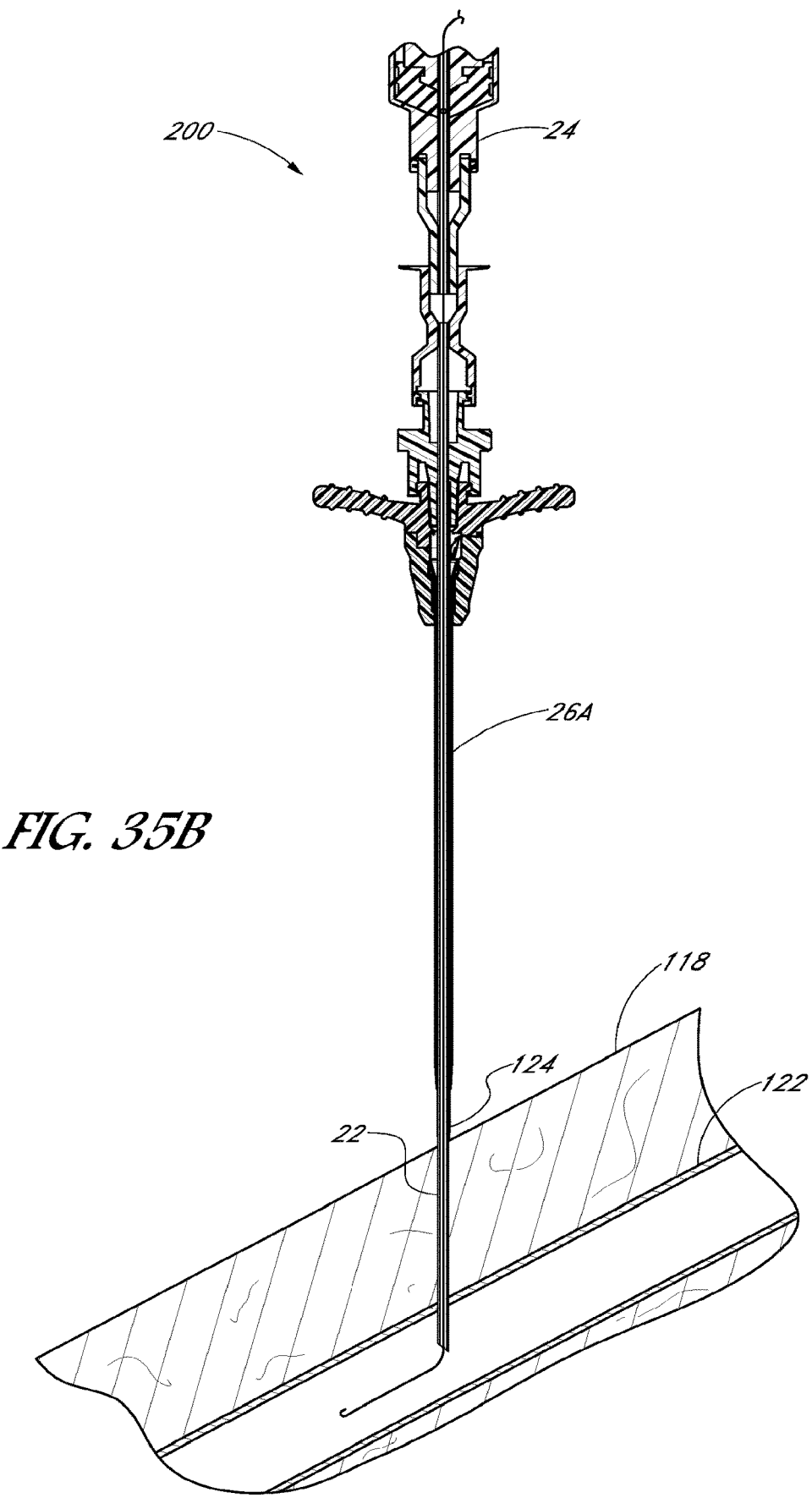
FIG. 35B is a cross-section view similar to FIG. 35A except the guide wire has been extended further into the vasculature of the patient.

FIG. 35A is a cross-section view similar to FIG. 34A except a guide wire 28 has been fed through the plunger 32, the valve 116, and needle 22 and into the blood vessel 122 of the patient. The dilator 124 and the sheath 26A have yet to penetrate the vasculature. Once the physician or healthcare provider has located the needle 22 within the target blood vessel 122, the physical or healthcare provider feeds the guide wire 28 through the plunger 32 while maintain the position of the plunger 32 relative to the barrel 30. Preferably the needle 22 is also held still while the guide wire 28 is fed through the syringe 24 and into the patient During the insertion procedure, the valve 116 seals against the guide wire 28 preventing air from entering the central channel 56 to maintain the negative pressure in the fluid chamber 34. A guide wire advancer as known in the art may be employed when feeding the guide wire 28 through the syringe 24. For example, if the guide wire 28 has a curved or J tip, an advancer may be employed to straighten the tip facilitating feeding of the guide wire 28 into the central channel 56 of the plunger 32. FIG. 35B is a cross-section view similar to FIG. 34A except the guide wire 28 has been extended further into the vasculature of the patient. The dilator 124 and the sheath 26A have yet to penetrate the vasculature.

Figure 36:
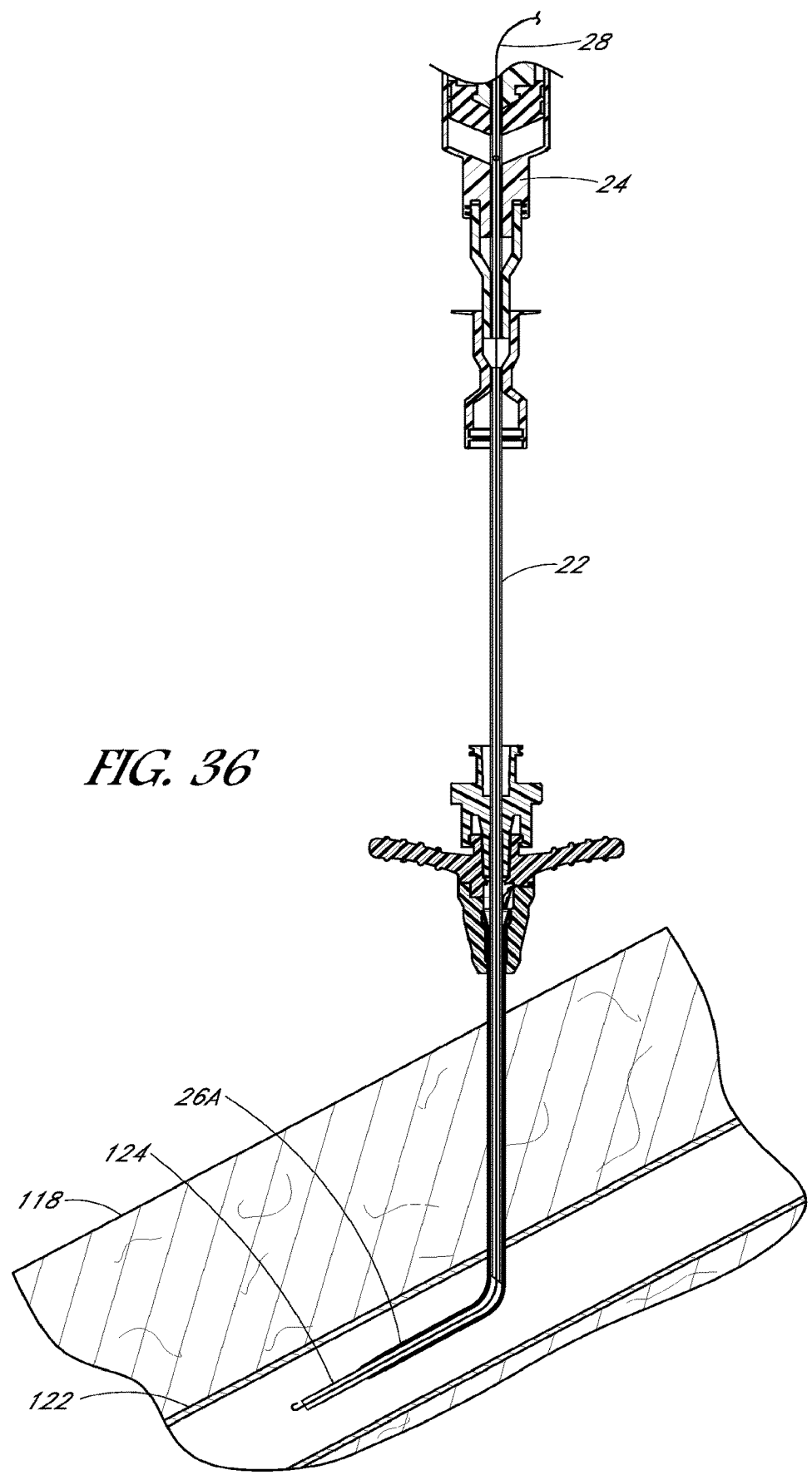
FIG. 36 is a cross-section view similar to FIG. 35B except the dilator and sheath have been slid along the exterior portion of the needle and into the patient's vasculature.

FIG. 36 is a cross-section view similar to FIG. 35B except the sheath 26A and the dilator 124 have been slid along the exterior portion 42 of the needle 22 and into the patient's vasculature. During insertion of the sheath 26A and dilator 124 over the needle 22 and guide wire 28 and into the blood vessel 122, the existing negative pressure in the syringe 24 ensures that any air located between an inside diameter of the sheath 26A and an outside diameter of the needle 22 and/or between an outside diameter of the dilator 124 and an inside diameter of the sheath 36A is drawn into the needle 22 rather than into the blood vessel 122. In addition to employing the dilator 124 in certain embodiments, a skinnick can be performed to enlarge the puncture site adjacent to the needle 22 facilitating insertion of the dilator 124 into the patient.

FIG. 37 is a cross-section view similar to FIG. 36 except the syringe 24 and the guide wire 28 have been removed from the patient leaving the dilator 124 and the sheath 26A in the vasculature. During the removal process, the internal volume of the stationary sheath 26A increases as the needle 22 and the guide wire 28 are removed which creates negative pressure in the sheath 26A ensuring air is not drawn into the blood vessel 122 during removal.

Figure 38:
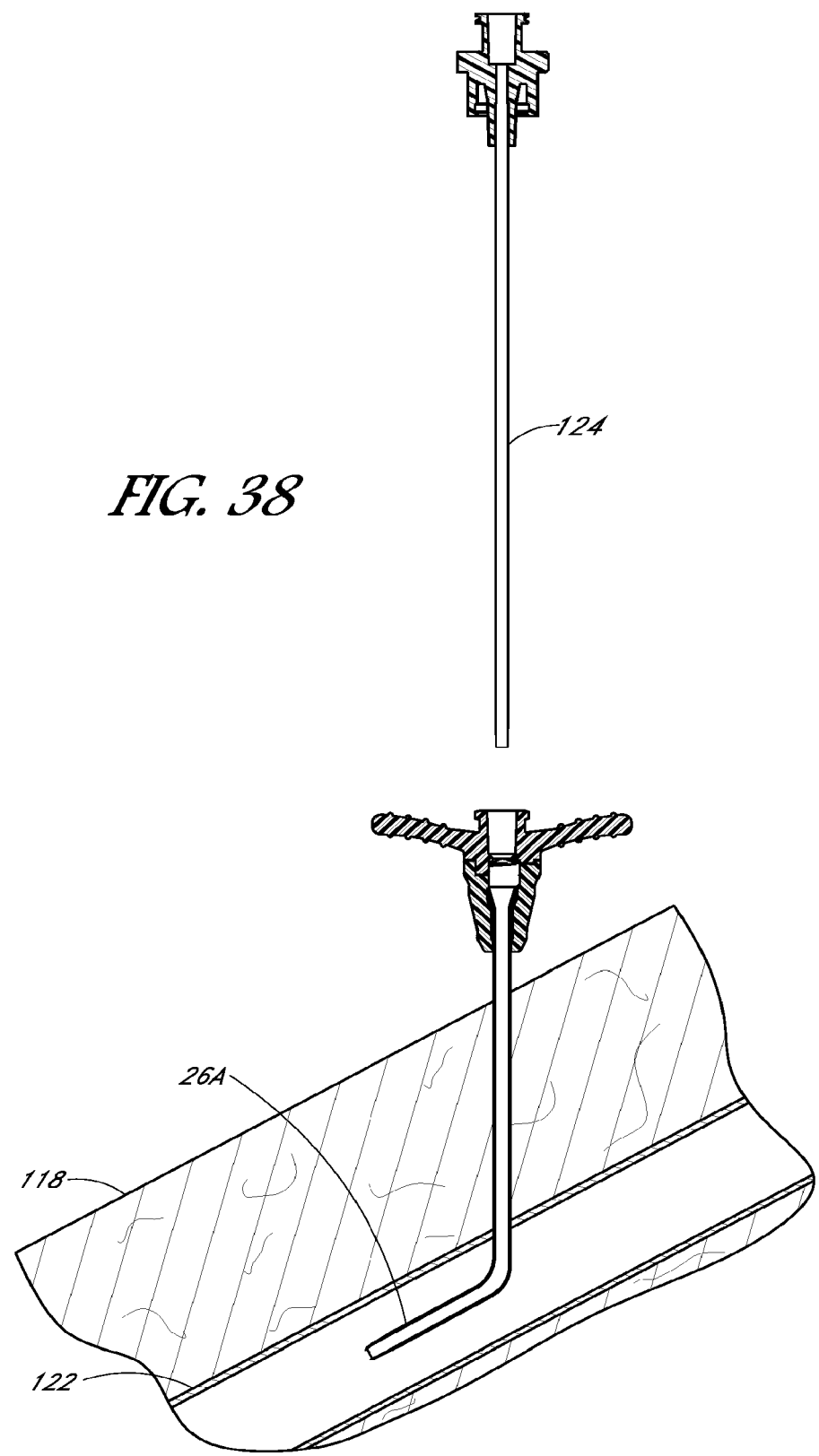
FIG. 38 is a cross-section view similar to FIG. 37 except the dilator has been removed from the patient and the sheath.

FIG. 38 is a cross-section view similar to FIG. 37 except the dilator 124 has been removed from the patient and the sheath 26A. The sheath 26A is left properly inserted within the blood vessel 122. The dilator 124 may be removed after the syringe 24 and the guide wire 28 are removed or in concert with removal of the syringe 24 and the guide wire 28. During the removal process, the internal volume of the stationary sheath 26A increases as the dilator 124 is removed which creates negative pressure in the sheath 26A ensuring air is not drawn into the blood vessel 122 during removal.

The described procedure is less tune intensive than the Raulerson syringe techniques and does not require multiple exchanges over the guide wire when employed with multiple medical articles (e.g., dilator over guide wire, sheath over guide wire, catheter over guide wire). If such exchanges were performed over the guide wire, such actions present the risk of losing cannulation, lost guide wire, and contamination. Further, during the skin-nick step the needle 22 protects the guide wire 28 from being accidently severed. The described technique reduces the risk of movement of the sheath 26, 26A and guide wire 28 relative to the patient during the procedure. The above described procedure is less bloody, especially if a valved sheath 26A is employed, and reduces the exposure of the physician or healthcare provider to blood.

Figure 40:
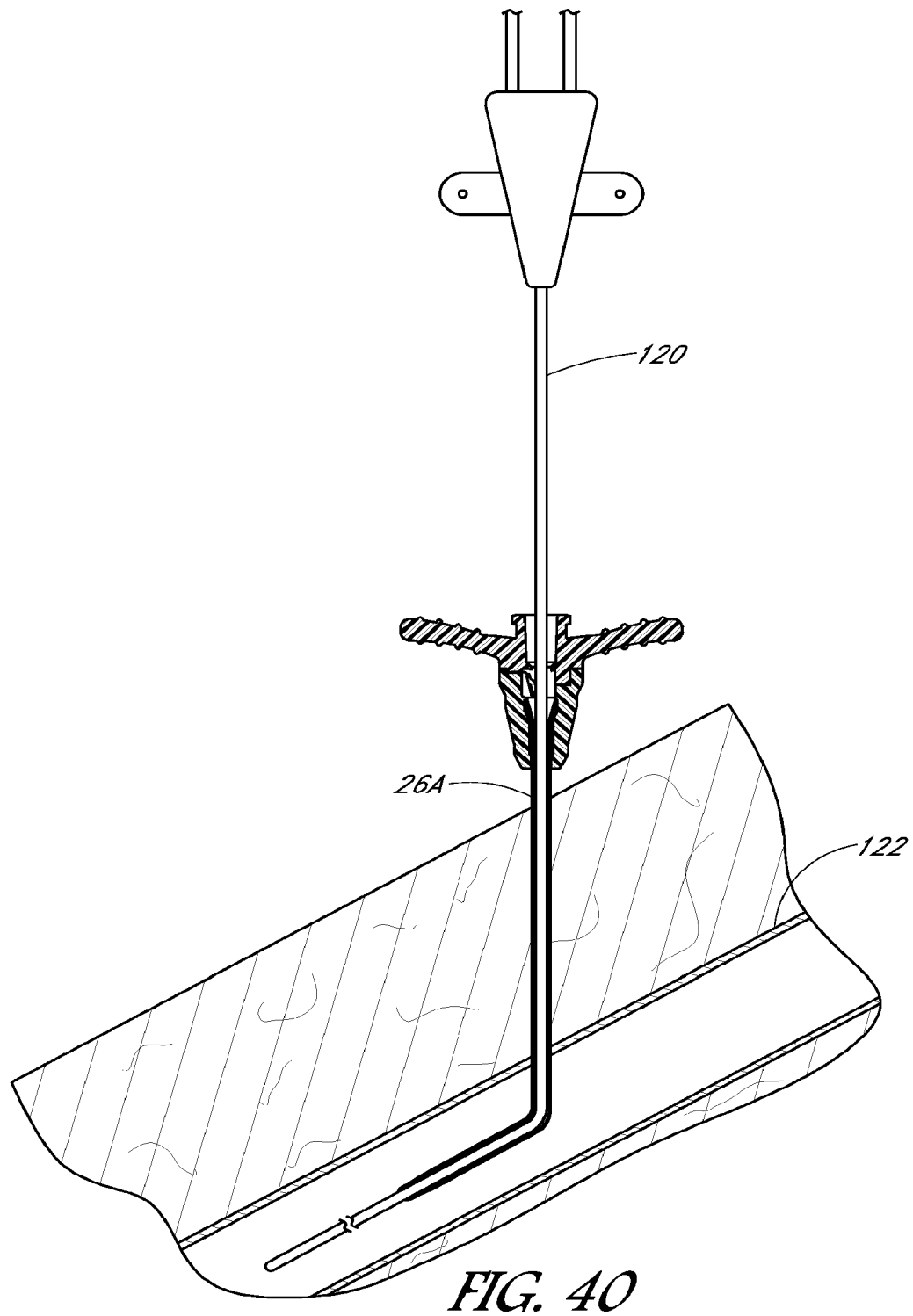
FIG. 40 is a cross-section view similar to FIG. 39 except the catheter has been inserted through the sheath and into the patient's vasculature.

FIG. 39 is a cross-section view similar to FIG. 38 except a catheter 120 is aligned with the sheath 26A for insertion into the patient's vasculature. FIG. 40 is a cross-section view similar to FIG. 39 except the catheter 120 has been inserted through the sheath 26A and into the patient's vasculature, specifically the targeted blood vessel 122.

Figure 41:
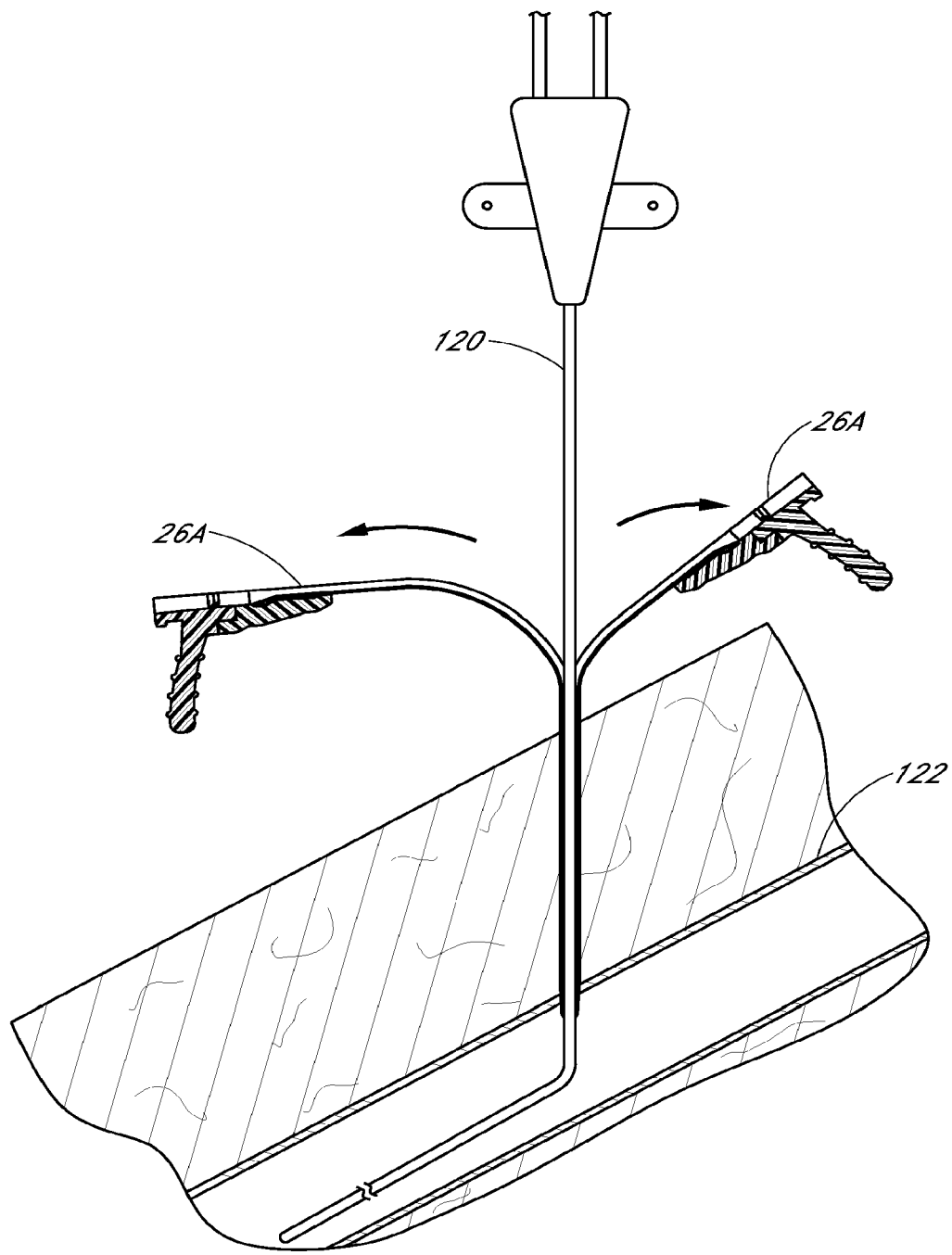
FIG. 41 is a cross-section view similar to FIG. 40 except two portions of the sheath are being peeled away from each other to remove the sheath from encircling the catheter.

FIG. 41 is a cross-section view similar to FIG. 40 except two portions of the sheath 26A are being peeled away from each other to remove the sheath 26A from encircling the catheter 120. The sheath 26A is splittable along one or more split lines 68, 68A (see FIGS. 4 and 5). A splittable sheath 26A provides the advantage of allowing a portion of or the entire sheath body 58 to be removed depending on the type of catheter or medical article that is to be inserted into the vessel after employing the access device 200. For example, after the catheter 120 is inserted into the blood vessel 122, a portion of the sheath body 58 is separated or peeled-away and removed to reduce clutter at the access site. The peel-away sheath 26A can be first slid in a proximal direction along the catheter 120 until the sheath 26A is removed from the patient and then split apart. Alternatively, the sheath 26A can be initially split prior to the entire sheath 26A being removed from the patient After the remainder of the sheath 26A is removed from the patient, the physician or healthcare provided can continue splitting the sheath 26A. Of course, the sheath 26A could be split in concert with its removal from the patient as is illustrated in FIG. 41. In certain embodiments, the sheath 26A is not splittable.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above.

What is claimed is:

1. An access device for placing a medical article within a body space, the access device comprising:
   a barrel and a plunger slidingly disposed in the barrel, the plunger having a channel sized and shaped to receive a guide wire therethrough, the barrel defining a fluid chamber;
   a plunger valve disposed in operative relationship relative to the channel to prevent passage of fluid through the channel during at least one operation performed from a group comprising flushing the access device and aspirating the access device;
   an interior needle portion at least partially disposed in the channel and comprising an aperture through a side wall of the interior needle portion and into the fluid chamber;
   a needle hub disposed on an exterior needle portion extending from the barrel and being in flow communication with the interior needle portion and the fluid chamber, the needle hub comprising a first locking structure and a second locking structure; and
   a sheath coaxially disposed about the exterior needle portion and slideable along the exterior needle portion, a distal end of the sheath being positioned proximal to a distal end of the exterior needle portion; and
   a dilator disposed about the exterior needle portion and within the sheath, the dilator comprising a dilator hub,
   wherein the first locking structure is configured to releasably secure the needle hub to the barrel, and
   wherein the second locking structure is configured to releasably secure the needle hub to the dilator hub.

2. The access device of claim 1, wherein the plunger valve is configured to seal against the guide wire disposed in the channel.

3. The access device of claim 1, wherein the plunger valve comprises one or more one-way valve elements.

4. The access device of claim 3, wherein the one or more one-way valve elements comprises a flexible resilient hollow hemisphere member.

5. The access device of claim 1, wherein the plunger valve is configured to prevent air from entering the channel during aspiration.

6. The access device of claim 1, wherein the sheath comprises a sheath body, a sheath hub, and a sheath valve, the sheath hub defining an inner cavity, wherein the sheath valve is disposed in the inner cavity to inhibit flow through the inner cavity in a proximal direction.

7. The access device of claim 6, wherein the sheath valve is configured to seal against the exterior needle portion.

8. The access device of claim 6, wherein the sheath valve is biased to prevent gas from being drawn distally through the inner cavity.

9. An access device for placing a medical article within a body space, the access device comprising:
   a syringe and a needle extending from the syringe, the syringe having a channel configured to receive a guide wire extending through the needle, the needle comprising a first locking structure and a second locking structure, wherein the syringe comprises a barrel and a plunger slidingly disposed in the barrel, wherein the plunger comprises a plunger channel configured to receive the guide wire;
   a plunger valve disposed in operative relationship relative to the plunger channel to prevent passage of fluid through the plunger channel during at least one operation performed from a group comprising flushing the access device and aspirating the access device;
   a sheath coaxially disposed about the needle and slideable along the needle; and
   a dilator disposed about the needle and within the sheath, wherein the first locking structure is configured to releasably secure the needle to the syringe, and
   wherein the second locking structure is configured to releasably secure the needle to the dilator.

10. The access device of claim 9, wherein the plunger valve is configured to seal against the guide wire disposed in the plunger channel.

11. The access device of claim 9, wherein the plunger valve comprises one or more one-way valve elements.

12. The access device of claim 11, wherein the one or more one-way valve elements comprises a flexible resilient hollow hemisphere member.

13. The access device of claim 9, wherein the plunger valve is configured to prevent air from entering the plunger channel during aspiration.

14. The access device of claim 9, wherein the sheath comprises a sheath body, a sheath hub, and a sheath valve, the sheath hub defining an inner cavity, wherein the sheath valve is disposed in the inner cavity to inhibit flow through the inner cavity in a proximal direction.

15. The access device of claim 14, wherein the sheath valve is configured to seal against the needle.

16. The access device of claim 14, wherein the sheath valve is biased to prevent gas from being drawn distally through the inner cavity.

17. A method for placing a medical article within a body space, the method comprising:
   penetrating a blood vessel with an access device, the access device comprising:
      a syringe and a needle extending from the syringe, the syringe having a channel configured to receive a guide wire extending through the needle, the needle comprising a first locking structure and a second locking structure, wherein the syringe comprises a barrel and a plunger slidingly disposed in the barrel, wherein the plunger comprises a plunger channel configured to receive the guide wire,
      a plunger valve disposed in operative relationship relative to the plunger channel to prevent passage of fluid through the plunger channel during at least one operation performed from a group comprising flushing the access device and aspirating the access device, and
      a sheath coaxially disposed about the needle and slideable along the needle,
      a dilator disposed about the needle and within the sheath,
      wherein the first locking structure is configured to releasably secure the needle to the syringe, and
      wherein the second locking structure is configured to releasably secure the needle to the dilator;
   feeding the guide wire through the channel, the needle, and into the blood vessel;
   sliding the sheath along the needle in a distal direction until at least a portion of the sheath is disposed in the blood vessel; and
   removing the syringe, the needle, and the guide wire from the blood vessel, leaving the sheath.

18. The method of claim 17, wherein the plunger valve is configured to seal against the guide wire disposed in the plunger channel.

19. The method of claim 17, wherein the plunger valve is configured to prevent air from entering the plunger channel during aspiration.

20. The method of claim 17, wherein the sheath comprises a sheath body, a sheath hub, and a sheath valve, the sheath hub defining an inner cavity, wherein the sheath valve is disposed in the inner cavity to inhibit flow through the inner cavity in a proximal direction.

21. The method of claim 20, wherein the sheath valve is configured to seal against the needle.

22. The method of claim 20, wherein the sheath valve is biased to prevent gas from being drawn distally through the inner cavity.

* * * * *